(12) United States Patent
Nakano et al.

(10) Patent No.: US 6,846,943 B2
(45) Date of Patent: Jan. 25, 2005

(54) METALLOCENE COMPOUND, OLEFIN POLYMERIZATION CATALYST CONTAINING THE COMPOUND, AND METHOD FOR PRODUCING AN OLEFIN POLYMER BY USE OF THE CATALYST

(75) Inventors: Masato Nakano, Ichihara (JP); Tsutomu Ushioda, Ichihara (JP); Hiroshi Yamazaki, Tokorozawa (JP); Toshihiro Uwai, Ichihara (JP); Masami Kimura, Ichihara (JP); Yoshiyuki Ohgi, Ichihara (JP); Kiyomi Yamamoto, Ichihara (JP)

(73) Assignee: Chisso Corporation, Osaki (JP)

( * ) Notice: Subject to any disclaimer, the term of this patent is extended or adjusted under 35 U.S.C. 154(b) by 67 days.

(21) Appl. No.: 09/861,726

(22) Filed: May 22, 2001

(65) Prior Publication Data

US 2001/0053833 A1 Dec. 20, 2001

(30) Foreign Application Priority Data

| May 23, 2000 | (JP) | ................................. | 2000-151673 |
| May 23, 2000 | (JP) | ................................. | 2000-151674 |
| Oct. 20, 2000 | (JP) | ................................. | 2000-321373 |
| Oct. 20, 2000 | (JP) | ................................. | 2000-321374 |
| Oct. 20, 2000 | (JP) | ................................. | 2000-321376 |

(51) Int. Cl.$^7$ .................................. C07F 17/00; C08F 4/64
(52) U.S. Cl. ..................... 556/53; 526/160; 526/743
(58) Field of Search ......................... 556/53; 526/160

(56) References Cited

U.S. PATENT DOCUMENTS

| 5,145,819 A | 9/1992 | Winter et al. |
| 5,585,509 A | 12/1996 | Langhauser et al. |
| 5,767,209 A | 6/1998 | McNally |
| 5,814,574 A | 9/1998 | McNally |
| 5,840,947 A | 11/1998 | Kuber et al. |
| 5,840,948 A | 11/1998 | Rohrmann et al. |
| 5,852,142 A | 12/1998 | Rohrmann et al. |
| 5,929,264 A | 7/1999 | Rohrmann et al. |
| 5,998,039 A | 12/1999 | Tanizaki et al. |
| 6,051,522 A | 4/2000 | Rohrmann et al. |
| 6,458,982 B1 * | 10/2002 | Schottek et al. |
| 6,479,646 B1 * | 11/2002 | Nakano et al. |

FOREIGN PATENT DOCUMENTS

| DE | 44 06 963 | 3/1994 |
| EP | 0 426 638 | 5/1991 |
| EP | 0 427 696 | 5/1991 |
| EP | 0 427 697 | 5/1991 |
| EP | 0 629 631 | 12/1994 |
| EP | 0 629 632 | 12/1994 |
| JP | 7-145212 | 6/1995 |
| JP | 7-149832 | 6/1995 |
| JP | 7-149833 | 6/1995 |
| JP | 7-258282 | 10/1995 |
| JP | 8-12715 | 1/1996 |
| JP | 8-73532 | 3/1996 |
| JP | 8-183814 | 7/1996 |
| JP | 8-283343 | 10/1996 |
| JP | 9-12635 | 1/1997 |
| JP | 10-265527 | 10/1998 |
| JP | 10-273507 | 10/1998 |
| JP | 11-171925 | 6/1999 |
| JP | 11-302470 | 11/1999 |
| JP | 11-335415 | 12/1999 |
| JP | 11-349649 | 12/1999 |
| WO | WO 88/05792 | 8/1988 |
| WO | WO 88/05793 | 8/1988 |
| WO | WO 92/00333 | 1/1992 |

OTHER PUBLICATIONS

L. Resconi, et al., "Selectivity in Propene Polymerization with Metallocene Catalysts", Chem. Rev., 2000, 100, (4), pp. 1253–1346.

Jennifer L. Maciejewski Petoff, et al., J. Am. Chem. Soc., vol. 120, No. 44, pp. 11316–11322, "Elastomeric Pollypropylene from Unabridged 2–Arylindenyl Zirconocenes: Modeling Polymerization Behavior Using Ansa–Metallocene Analogues", 1998.

(List continued on next page.)

Primary Examiner—Caixia Lu
(74) Attorney, Agent, or Firm—Oblon, Spivak, McClelland, Maier & Neustadt, P.C.

(57) ABSTRACT

The present invention provides a metallocene compound which produces an olefin polymer having a high molecular weight with a high stereoregularity. The metallocene compound has the following formula (1):

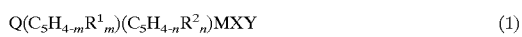

$$Q(C_5H_{4-m}R^1_m)(C_5H_{4-n}R^2_n)MXY \qquad (1)$$

wherein $(C_5H_{4-m}R^1_m)$ and $(C_5H_{4-n}R^2_n)$ each independently represent a cyclopentadienyl group;
$C_5H_{4-m}$ and $C_5H_{4-n}$ each independently represent a cyclopentadienyl ring;
m represents an integer of 1–3;
n represents an integer of 2 or 3;
$R^1$ and $R^2$ are each independently a substituent bonded respectively to $C_5H_{4-m}$ and $C_5H_{4-n}$, and represent a hydrocarbon group of 1–20 carbon atoms, a silicon-containing hydrocarbon group of 1–20 carbon atoms or a heteroaromatic group;
each $R^1_m$ and each $R^2_n$ may be the same or different;
one pair of $R^2$'s in the $R^2_n$ are bonded to each other to form at least one ring;
Q represents a divalent group for cross-linking $(C_5H_{4-m}R^1_m)$ and $(C_5H_{4-n}R^2_n)$;
M represents a titanium atom, a zirconium atom or a hafnium atom; and
X and Y are the same or different and each a hydrogen atom, a halogen atom or a hydrocarbon group.

9 Claims, No Drawings

OTHER PUBLICATIONS

John A. Ewen, et al., J. Am. Chem. Soc., vol. 120, No. 41, pp. 10786–10787, "Polymerization Catalysts with Cyclopentadienyl Ligands Ring–Fused to Pyrrole and Thiophene Heterocycles", 1998.

Toshihiko Sugano, et al., SPO '99, pp. 31–53, "Novel Metallocene Catalyst for Propylene Polymerization", 1999.

A. Zambelli, et al., Communications to the Editor, Macromolecules, vol. 6, No. 6, pp. 925–926, "Carbon–13 Observations of the Stereochemical Configuration of Polypropylene", Nov.–Dec. 1973.

A. Zambelli, et al., Communications to the Editor, Macromolecules, vol. 8, No. 5, pp. 687–689, "Model Compounds and $^{13}$C NMR Observation of Stereosequences of Polypropylene", Sep.–Oct. 1975.

Toshiyuki Tsutsui, et al., Polymer, vol. 30, pp. 1350–1356, "Propylene Homo– and Copolymerization with Ethylene Using an Ethylenebis(1–Indenyl)Zirconium Dichloride and Methylaluminoxane Catalyst System", Jul. 1989.

* cited by examiner

METALLOCENE COMPOUND, OLEFIN POLYMERIZATION CATALYST CONTAINING THE COMPOUND, AND METHOD FOR PRODUCING AN OLEFIN POLYMER BY USE OF THE CATALYST

FIELD OF THE INVENTION

This invention relates to a novel metallocene compound useful as an olefin polymerization catalyst and more particularly to a specific metallocene compound having a specific heteroaromatic group. Further, this invention relates to an olefin polymerization catalyst containing the metallocene compound and a method for producing an olefin polymer by the use of the catalyst.

BACKGROUND OF THE INVENTION

Metallocene compounds, i.e., compounds having a transition metal atom coordinated with a multidentate compound containing a π-electron donating group such as an unsubstituted or substituted cycloalkadienyl group, for example, an unsubstituted or substituted cyclopentadienyl group, an unsubstituted or substituted indenyl group, an unsubstituted or substituted tetrahydroindenyl group, and an unsubstituted or substituted fluorenyl group have been partly used in the place of the Ziegler-Natta catalyst which has been heretofore used for the polymerization of an olefin.

Particularly in recent years, various metallocene compounds showing increasingly high olefin polymerization activity per mol of a transition metal atom have been proposed. For example, a chiral metallocene compound which has a transition metal atom coordinated with a multidentate compound having two substituted cycloalkadienyl groups cross-linked with a divalent linking group has been proposed (J. Am. Soc. 1998, 120, 11316–11322). It has been reported that α-olefin polymers of not less than three carbon atoms, particularly a propylene polymer, polymerized by the use of this compound as a catalyst has a high stereoregularity.

Further, the development of metallocene compounds showing a high polymerization activity in the polymerization of olefins is being continued. Then, various metallocene compounds incorporating therein heteroatoms as a constituent for forming a substituent to be bonded to a cycloalkadienyl ring or forming a cycloalkadiene ring itself have been proposed.

U.S. Pat. No. 5,585,509 (DE 4406963, JP-A-7-258282), for example, discloses a metallocene compound having an indenyl group in which a hydrogen at the 2-position of the indenyl group is replaced by a saturated group containing a heteroatom such as a nitrogen atom, a phosphorus atom, an arsenic atom, an antimony atom and a bismuth atom, specifically a metallocene compound obtained by cross-linking two 2-pyrrolidino-1-indene with a divalent linking group and coordinating it to a transition metal atom.

Then, JP-A-8-183814 discloses a metallocene compound having an indenyl group in which a hydrogen at the 4-position of the indenyl group is replaced by a 1-pyrrolyl group, a 1-indolyl group, etc., specifically a chiral metallocene compound obtained by cross-linking two 4-(1-indolyl)-2-methyl-indenes with a divalent linking group and coordinating it to a transition metal atom.

Further, J. Am. Chem. Soc. 1998, 120, 10786–10787 discloses a metallocene compound obtained by cross-linking with a divalent linking group two heteroatom-containing cycloalkadienes, each having a thiophene ring or a pyrrol ring condensed with a cyclopentadiene ring, and coordinating it to a transition metal atom.

U.S. Pat. No. 5,840,947 (DE 19517851, JP-A-8-333379) discloses a metallocene compound having a pyridyl group, quinolyl group, etc. as a substituent.

These metallocene compounds generally have mainly been developed with a view to producing a high molecular weight olefin polymer and controlling a stereoregularity of the produced olefin polymer to a high degree.

When a propylene/ethylene copolymer is produced by using a metallocene catalyst, however, the molecular weight of the produced copolymer is generally lowered to no small extent in proportion to the amount of ethylene in the copolymer as compared with that of a propylene homopolymer (T. Sugano, SPO '99, 31–53 (1999). Even in the production of such a copolymer, therefore, development of a metallocene compound capable of producing the copolymer having a high molecular weight has been desired.

As the olefin polymer having a controlled stereoregularity, JP-A-10-273507 has reported a highly stereoregular propylene polymer, wherein (A) the isotactic triad ratio of the propylene unit chain part formed by head-tail bonds is not less than 97% as determined by the method of $^{13}$C-NMR nuclear magnetic resonance spectrum analysis ($^{13}$C-NMR); (B) the proportion of the propylene units originating from 2,1-insertion of the propylene monomer in the whole propylene units is in the range of 0.5–2.0 mol % and the proportion of the propylene units originating from 1,3-insertion of the propylene monomer is in the range of 0.06–0.4 mol %, as determined by the $^{13}$C-NMR; and (C) the weight average molecular weight, Mw is in the range of 10,000–1,000,000 as determined by the gel permeation chromatography (GPC).

JP-A-11-171925 has reported a highly stereoregular propylene polymer, wherein (A) the isotactic triad ratio of the propylene unit chain part formed by head-tail bonds is not less than 98% as determined by the $^{13}$C-NMR; (B) the proportion of the propylene units originating from 2,1-insertion of the propylene monomer in the whole propylene units is not more than 0.03 mol % and the proportion of the propylene units originating from 1,3-insertion of the propylene monomer is not less than 0.06 mol %, as determined by the $^{13}$C-NMR; (C) the weight average molecular weight is in the range of 10,000–1,000,000; and (D) the melting point is not lower than 160° C.

Then, JP-A-7-145212 has reported a propylene polymer having a high stiffness and a high heat resistance, wherein (A) the triad tacticity of the propylene unit chain part formed by head-tail bonds is not less than 90.0% as determined by the $^{13}$C-NMR; (B) the proportion of the propylene units originating from 2,1-insertion of the propylene monomer in the whole propylene units is not less than 0.7 mol % and the proportion of the propylene units originating from 1,3-insertion of the propylene monomer is not more than 0.05 mol %, as determined by the $^{13}$C-NMR; and (C) the intrinsic viscosity is in the range of 0.1–12 dl/g as determined in decalin at 135° C.

Further, JP-A-7-149832 has reported a propylene copolymer having a high stiffness and a high heat resistance, wherein (A) the content of a propylene unit is in the range of 95–99.5 mol % and that of an ethylene unit is in the range of 0.5–5 mol %; (B) the triad tacticity of the propylene unit chain part formed by head-tail bonds is not less than 90.0% as determined by the $^{13}$C-NMR; (C) the proportion of the propylene units originating from 2,1-insertion of the propylene monomer in the whole propylene units is not less than 0.5 mol % and the proportion of the propylene units originating from 1,3-insertion of the propylene monomer is not more than 0.05 mol %, as determined by the $^{13}$C-NMR; and (D) the intrinsic viscosity is in the range of 0.1–12 dl/g as determined in decalin at 135° C.

SUMMARY OF THE INVENTION

However, it has been difficult to produce, by using a metallocene compound as a catalyst, an olefin polymer having a stereoregularity controlled to a very high degree so that the proportion of the propylene units originating from 2,1-insertion and the proportion of the propylene units originating from 1,3-insertion are both less than 0.05 mol % in the whole propylene units forming the olefin polymer.

An object of the present invention is therefore to provide a metallocene compound capable of producing an olefin polymer having a high molecular weight and having a stereoregularity controlled to an extremely high degree, a metallocene catalyst comprising the metallocene compound, and a method for producing an olefin polymer by the use of the catalyst. This invention further provides a metallocene compound capable of producing an olefin polymer having a high polymerization activity, high yield of polymerization, a high molecular weight and a stereoregularity controlled to an extremely high degree, a metallocene catalyst comprising the metallocene compound, and a method for producing an olefin polymer by the use of the catalyst.

The present inventors have studied the structure of a metallocene compound and the connection between the molecular weight and the stereoregularity of the produced olefin polymer with a view to accomplishing the objects mentioned above, and have found that the objects of this invention are accomplished by using a specific metallocene compound having a specific heteroaromatic group.

Specifically, this invention provides a metallocene compound represented by the following formula (1):

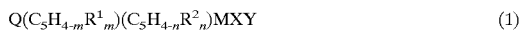

wherein $(C_5H_{4-m}R^1_m)$ and $(C_5H_{4-n}R^2_n)$ each independently represent a cyclopentadienyl group;
$C_5H_{4-m}$ and $C_5H_{4-n}$ each independently represent a cyclopentadienyl ring;
m represents an integer in the range of 1–3;
n represents an integer of 2 or 3;
$R^1$ and $R^2$ are each independently a substituent bonded respectively to $C_5H_{4-m}$ and $C_5H_{4-n}$, and represent a hydrocarbon group of 1–20 carbon atoms, a silicon-containing hydrocarbon group of 1–20 carbon atoms, or a heteroaromatic group which is selected from the group consisting of an unsubstituted heteroaromatic ring and a heteroaromatic ring having at least one substituent bonded to the ring, the substituent being a hydrocarbon group of 1–20 carbon atoms or a silicon-containing hydrocarbon group of 1–20 carbon atoms;
each $R^1_m$ and each $R^2_n$ may be the same or different;
one pair of $R^2$'s in the $R^2_n$ are bonded to each other to form at least one ring;
one pair of $R^1$'s in the $R^1_m$ may be bonded to each other to form at least one ring, when m is an integer of 2 or 3;
the ring formed by the pair of $R^1$'s and the ring formed by the pair of $R^2$'s each may independently have at least one substituent bonded to the ring, wherein the substituent is a hydrocarbon group of 1–20 carbon groups, a silicon-containing hydrocarbon group of 1–20 carbon groups, or a heteroaromatic group selected from the group consisting of an unsubstituted heteroaromatic ring and a heteroaromatic ring having at least one substituent bonded to the ring, the substituent being a hydrocarbon group of 1–20 carbon atoms or a silicon-containing hydrocarbon group of 1–20 carbon groups;
provided that at least one substituent selected from the group consisting of the substituents $R^1_m$ and $R^2_n$, the substituent(s) bonded to the ring formed by the one pair of $R^1$'s, and the substituent(s) bonded to the ring formed by the one pair of $R^2$'s is a heteroaromatic group having a heteroaromatic ring and at least one substituent bonded to the heteroaromatic ring, the substituent being a hydrocarbon group of 1–20 carbon atoms or a silicon-containing hydrocarbon group of 1–20 carbon atoms;
Q represents a divalent group for cross-linking $(C_5H_{4-m}R^1_m)$ and $(C_5H_{4-n}R^2_n)$, and is a hydrocarbon group, an unsubstituted silylene group, a hydrocarbon-substituted silylene group, or a boron compound having a $R^3_2NB$ structure, wherein $R^3$ represents a hydrocarbon group of 1–20 carbon atoms, a silicon-containing hydrocarbon group of 1–20 carbon atoms or a heteroaromatic group;
M represents a titanium atom, a zirconium atom, or a hafnium atom; and
X and Y are the same or different and each are a hydrogen atom, a halogen atom or a hydrocarbon group.

This invention also provides the metallocene compound of the formula (1), wherein n is the integer of 3, the $R^2$ other than the pair of $R^2$'s bonded to each other to form at least one ring is a heteroaromatic group, which has a heteroaromatic ring and at least one substituent bonded to said heteroaromatic ring, the substituent being a hydrocarbon group of 1–20 carbon atoms or a silicon-containing hydrocarbon group of 1–20 carbon atoms.

This invention also provides the metallocene compound of the formula (1), wherein n is the integer of 3, the $R^2$ other than the pair of $R^2$'s bonded to each other to form at least one ring is bonded at the 2-position of a cyclopentadienyl ring $C_5H_{4-n}$.

This invention further provides the metallocene compound of the formula (1), wherein the structure not having a plane of symmetry containing M is formed because of either the difference between $R^1$ and $R^2$ or the difference in the positions at which $R^1$ and $R^2$ are bonded to a cyclopentadienyl ring, or both.

Further, this invention provides the metallocene compound of the formula (1), wherein at least one substituent selected from the group consisting of the substituents $R^1_m$ and $R^2_n$, the substituent(s) bonded to the ring formed by said one pair of $R^1$'s, and the substituent(s) bonded to the ring formed by said one pair of $R^2$'s is a heteroaromatic group which has a heteroaromatic ring and at least one of substituent bonded to said heteroaromatic ring, the substituent being a hydrocarbon group of 1–20 carbon atoms or a silicon-containing hydrocarbon group of 1–20 carbon atoms, and the heteroaromatic ring being a 2-furyl ring, a 2-thienyl ring, a 2-benzofuryl ring or a 2-benzothienyl ring.

This invention further provides the metallocene compound of the formula (1), wherein at least one substituent selected from the group consisting of the substituents $R^1_m$ and $R^2_n$, the substituent(s) bonded to the ring formed by said one pair of $R^1$'s, and the substituent(s) bonded to the ring formed by said one pair of $R^2$'s is a 2-(5-methyl)-furyl group, a 2-(5-t-butyl)-furyl group, a 2-(5-trimethylsilyl)-furyl group, a 2-(5-phenyl)-furyl group, a 2-(5-methyl)-thienyl group, a 2-(5-t-butyl)-thienyl group, a 2-(5-trimethylsilyl)-thienyl group, a 2-(5-phenyl)-thienyl group, a 2-(4,5-dimethyl)-furyl group, a 2-(4,5-dimethyl)-thienyl group, a 2-benzofuryl group or a 2-benzothienyl group.

This invention also provides the metallocene compound of the formula (1), which is selected from the group consisting of dimethylsilylene bis(2-(2-(5-methyl)-furyl)-indenyl) zirconium dichloride, dimethylsilylene bis(2-(2-(5-t-butyl)-furyl)-indenyl) zirconium dichloride, dimethylsilylene bis(2-(2-(5-trimethylsilyl)-furyl)-indenyl zirconium dichloride, dimethylsilylene bis(2-(2-(5-phenyl)-furyl)-indenyl) zirconium dichloride, dimethylsilylene bis(2-(2-(5-methyl)-thienyl)-indenyl) zirconium dichloride, dimethylsilylene bis-(2-(2-(5-t-butyl)-thienyl)-indenyl) zirconium dichloride, dimethylsilylene bis(2-(2-(5-trimethylsilyl)-thienyl)-indenyl) zirconium dichloride, dimethylsilylene bis-(2-(2-(5-phenyl)-thienyl)-indenyl) zirconium dichloride, dimethylsilylene bis(2-(2-(5-methyl)-furyl)-4-phenyl-indenyl) zirconium dichloride, dimethylsilylene bis(2-(2-(5-t-butyl)-furyl)-4-phenyl-indenyl) zirconium dichloride, dimethylsilylene bis(2-(2-(5-trimethylsilyl)-furyl)-4-phenyl-indenyl) zirconium dichloride, dimethylsilylene bis(2-(2-(5-phenyl)-furyl)-4-phenyl-indenyl) zirconium dichloride, dimethylsilylene bis (2-(2-(5-methyl)-thienyl)-4-phenyl-indenyl) zirconium dichloride, dimethylsilylene bis(2-(2-(5-t-butyl)-thienyl)-4-phenyl-indenyl) zirconium dichloride, dimethylsilylene bis (2-(2-(5-trimethylsilyl)-thienyl)-4-phenyl-indenyl) zirconium dichloride, dimethylsilylene bis(2-(2-(5-phenyl)-thienyl)-4-phenyl-indenyl) zirconium dichloride, dimethylsilylene bis(2-(2-(5-methyl)-furyl)-4,5-benzoindenyl) zirconium dichloride, dimethylsilylene bis(2-(2-(5-t-butyl)-furyl)-4,5-benzoindenyl) zirconium dichloride, dimethylsilylene bis(2-(2-(5-trimethylsilyl)-furyl)-4,5-benzoindenyl) zirconium dichloride, dimethylsilylene bis(2-(2-(5-phenyl)-furyl)-4,5-benzoindenyl) zirconium dichloride, dimethylsilylene bis(2-(2-(5-methyl)-thienyl)-4,5-benzoindenyl) zirconium dichloride, dimethylsilylene bis(2-(2-(5-t-butyl)-thienyl)-4,5-benzoindenyl) zirconium dichloride, dimethylsilylene bis(2-(2-(5-trimethylsilyl)-thienyl)-4,5-benzoindenyl) zirconium dichloride, dimethylsilylene bis(2-(2-(5-phenyl)-thienyl)-4,5-benzoindenyl) zirconium dichloride, dimethylsilylene bis(2-(2-(5-methyl)-furyl)-4-phenyl-dihydroazulenyl) zirconium dichloride, dimethylsilylene bis(2-(2-(5-t-butyl)-furyl)-4-phenyl-dihydroazulenyl) zirconium dichloride, dimethylsilylene bis(2-(2-(5-trimethylsilyl)furyl)-4-phenyl-dihydroazulenyl) zirconium dichloride, dimethylsilylene bis(2-(2-(5-phenyl)-furyl)-4-phenyl-dihydroazulenyl) zirconium dichloride, dimethylsilylene bis(2-(2-(5-methyl)-thienyl)-4-phenyl-dihydroazulenyl) zirconium dichloride, dimethylsilylene bis(2-(2-(5-t-butyl)-thienyl)-4-phenyl-dihydroazulenyl) zirconium dichloride, dimethylsilylene bis (2-(2-(5-trimethylsilyl)-thienyl)-4-phenyl-dihydroazulenyl) zirconium dichloride and dimethylsilylene bis(2-(2-(5-phenyl)-thienyl)-4-phenyl-dihydroazulenyl) zirconium dichloride.

This invention also provides an olefin polymerization catalyst comprising the aforementioned metallocene compound and an activating compound. This olefin polymerization catalyst may contain an organoaluminum compound, if necessary.

This invention also provides an olefin polymerization catalyst comprising a supported catalyst and an organoaluminum compound, in which the supported catalyst comprises the aforementioned metallocene compound, an activating compound and a support in the form of fine particles, and, if necessary, an organoaluminum compound.

This invention also provides an olefin polymerization catalyst comprising a supported catalyst and an organoaluminum compound, in which the supported catalyst comprises the aforementioned metallocene compound, and an ion-exchangeable layer compound or an inorganic silicate, and, if necessary, an organoaluminum compound.

This invention also provides a method for producing an olefin polymer by the use of the aforementioned olefin polymerization catalyst.

This invention further discloses a method for producing the olefin polymer mentioned above, wherein the olefin polymer is a propylene homopolymer or a propylene/olefin copolymer of propylene and an olefin other than propylene and containing not less than 50% by weight of propylene unit based on the weight of the copolymer.

This invention also discloses a method for producing an olefin polymer, wherein the proportion of the number of moles of a propylene unit originating from 2,1-insertion of the propylene monomer and that of the number of moles of a propylene unit originating from 1,3-insertion of the propylene monomer are each less than 0.05 mol %, based on the total number of moles of the propylene unit forming the olefin polymer.

According to this invention, the catalyst based on the aforementioned specific metallocene compound can produce olefin polymers having a high molecular weight and a stereoregularity precisely controlled to a high degree. Further, the aforementioned specific metallocene compound can be easily synthesized in a high yield through fewer synthesis steps. The amount of dl isomer (racemic isomer) formed during the synthesis is larger than that of meso isomer and, in particular, the cost for the synthesis of the dl isomer (racemic isomer) can be greatly reduced.

DETAILED DESCRIPTION OF THE INVENTION

Now, this invention will be described in detail below based on preferred embodiments.
Metallocene Compound The metallocene compounds of this invention are represented by the following formula (1):

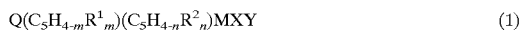

$$Q(C_5H_{4-m}R^1_m)(C_5H_{4-n}R^2_n)MXY \qquad (1)$$

In the formula (1), $(C_5H_{4-m}R^1_m)$ and $(C_5H_{4-n}R^2_n)$ each independently represent a cyclopentadienyl group, $C_5H_{4-m}$ and $C_5H_{4-n}$ each represent a cyclopentadienyl ring, m represents an integer in the range of 1–3, preferably a integer of 3, and n represents an integer of 2 or 3, independently of m, preferably the integer of 3.

$R^1$ and $R^2$ are each independently substituents bonded respectively to $C_5H_{4-m}$ and $C_5H_{4-n}$, and represent a hydrocarbon group of 1–20 carbon atoms, a silicon-containing hydrocarbon group of 1–20 carbon atoms or a heteroaromatic group. Each $R^1$ of the $R^1_m$ and each $R^2$ of the $R^2_n$ are each independently the same or different.

Concrete examples of the hydrocarbon group of 1–20 carbon atoms include a methyl group, an ethyl group, an n-butyl group, an isobutyl group, a t-butyl group, an n-hexyl group, an n-octyl group, a cyclohexyl group and a phenyl group. A methyl group, a t-butyl group and a phenyl group are particularly preferable.

A preferred example of the silicon-containing hydrocarbon group of 1–20 carbon atoms is a trimethylsilyl group.

The heteroaromatic group has a heteroaromatic ring and, if necessary, at least one substituent bonded to the ring.

The heteroaromatic ring used herein has a monocyclic or polycyclic structure. A monocyclic or bicyclic heteroaromatic ring is preferable. A monocyclic heteroaromatic ring is particularly preferable.

The heteroatom which a heteroaromatic ring contains is not particularly limited. The heteroaromatic ring containing an oxygen atom or a sulfur atom as the heteroatom is preferable and the heteroaromatic ring containing an oxygen atom is particularly preferable. Specifically, preferred aromatic rings are a furyl ring, a thienyl ring, a benzofuryl ring and a benzothienyl ring. More preferred are a 2-furyl ring, a 2-thienyl ring, a 2-benzofuryl ring and a 2-benzothienyl ring, and particularly preferable is a 2-furyl ring.

The substituent which may optionally be bonded to the heteroaromatic ring is a hydrocarbon group of 1–20 carbon atoms or a silicon-containing hydrocarbon group of 1–20 carbon atoms. Concrete examples of the hydrocarbon group of 1–20 carbon atoms and the silicon-containing hydrocarbon group of 1–20 carbon atoms are the same hydrocarbon groups and silicon-containing hydrocarbon groups as enumerated above as the substituents bonded respectively to the $C_5H_{4-m}$ and the $C_5H_{4-n}$.

The heteroaromatic group preferably has a heteroaromatic ring and at least one substituent bonded to the ring. Concrete examples of the heteroaromatic group include those having a furyl ring, a thienyl ring, a benzofuryl ring or a benzothienyl ring as the heteroaromatic ring, and a methyl group, an ethyl group, an n-butyl group, an isobutyl group, a t-butyl group, a phenyl group or a trimethylsilyl group as the substituent bonded to the ring. Preferably, heteroaromatic groups have a 2-furyl ring, a 2-thienyl ring, a 2-benzofuryl ring or a 2-benzothienyl ring as the heteroaromatic ring, and a methyl group, a t-butyl group, a phenyl group or a trimethysilyl group as the substituent bonded to the ring. Concrete examples of the heteroaromatic group include a 2-(5-methyl)-furyl group, a 2-(5-t-butyl)-furyl group, a 2-(5-trimethylsilyl)-furyl group, a 2-(5-phenyl)-furyl group, a 2-(5-methyl)-thienyl group, a 2-(5-t-butyl)-thienyl group, a 2-(5-trimethylsilyl)-thienyl group, a 2-(5-phenyl)-thienyl group, a 2-(4,5-dimethyl)-furyl group, a 2-(4,5-dimethyl)-thienyl group, a 2-benzofuryl group and a 2-benzothienyl group.

A pair of $R^2$'s in the $R^2_n$ are bonded to each other to form a monocyclic ring or a polycyclic ring. Though the number of rings is not particularly limited, it is preferably in the range of 1–5, particularly preferably 1 or 2. Preferred examples of the cyclic structure which the monocyclic ring or the polycyclic ring by the pair of $R^2$'s forms with the cyclopentadienyl ring $C_5H_{4-n}$, are an indenyl ring, a tetrahydroindenyl ring, a benzoindenyl ring, a dihydroazulenyl ring, and a cyclopentaphenanthrene ring, and more preferred examples thereof are an indenyl ring, a benzoindenyl ring and a dihydroazulenyl ring.

When m is 2 or 3, one pair of $R^1$'s in the $R^1_m$ may be bonded to each other to form at least one (monocyclic or polycyclic) ring, independently of the ring formed by the aforementioned pair of $R^2$'s. Preferred examples of the cyclic structure which the ring formed by the pair of $R^1$'s forms with the cyclopentadienyl ring $C_5H_{4-m}$ are an indenyl ring, a tetrahydroindenyl ring, a benzoindenyl ring, a dihydroazulenyl ring and a cyclopentaphenanthrene ring, and more preferred examples thereof are an indenyl ring, a benzoindenyl ring and a dihydroazulenyl ring.

The ring formed by the pair of $R^1$'s and the ring formed by the pair, of $R^2$'s may be the same or different. The cyclic structure which the ring formed by the pair of $R^1$'s forms with $C_5H_{4-m}$ is preferably an indenyl ring, a benzoindenyl ring or a dihydroazulenyl ring, and the cyclic structure which the ring formed by the aforementioned pair of $R^2$'s forms with $C_5H_{4-n}$ is preferably an indenyl ring, a benzoindenyl ring or a dihydroazulenyl ring. More preferably, both the cyclic structure which the ring formed by the pair of $R^1$'s forms with $C_5H_{4-m}$ and the cyclic structure which the ring formed by the pair of $R^2$'s forms with $C_5H_{4-n}$ are an indenyl ring, a benzoindenyl ring or a dihydroazulenyl ring.

The ring formed by the pair of $R^1$'s and the ring formed by the pair of $R^2$'s may each independently have at least one substituent respectively bonded to the rings. The substituent bonded to each ring is a hydrocarbon group of 1–20 carbon atoms, a silicon-containing hydrocarbon group or a heteroaromatic group.

Concrete examples of the hydrocarbon group of 1–20 carbon atoms include a methyl group, an ethyl group, an n-butyl group, an isobutyl group, a t-butyl group, an n-hexyl group, an n-octyl group, a cyclohexyl group and a phenyl group. More preferred examples thereof are a methyl group, a t-butyl group and a phenyl group.

A trimethylsilyl group is a preferred example of the silicon-containing hydrocarbon group of 1–20 carbon atoms.

The heteroaromatic group has a heteroaromatic ring and, if necessary, at least one substituent bonded to the ring.

The heteroaromatic ring which has a monocyclic or polycyclic structure is used herein. Preferably, it is a monocyclic or bicyclic heteroaromatic ring. Particularly preferably, it is a monocyclic heteroaromatic ring.

Then, the heteroatom which the heteroaromatic ring contains is not particularly limited. Preferably, the heteroaromatic ring contains an oxygen atom or a sulfur atom as the heteroatom. Particularly preferably, the heteroaromatic ring contains an oxygen atom as the heteroatom. Concrete examples of the preferred heteroaromatic ring include a furyl ring, a thienyl ring, a benzofuryl ring and a benzothienyl ring. More preferable heteroaromatic rings are a 2-furyl ring, a 2-thienyl ring, a 2-benzofuryl ring and a 2-benzothienyl ring. A particularly preferred heteroaromatic ring is a 2-furyl ring.

The substituent which may optionally be bonded to the heteroaromatic ring is a hydrocarbon group of 1–20 carbon atoms or a silicon-containing hydrocarbon group of 1–20 carbon atoms. Concrete examples of the hydrocarbon group of 1–20 carbon atoms and the silicon-containing hydrocarbon group of 1–20 carbon atoms may be the same as those cited above as concrete examples of the substituents respectively bonded to $C_5H_{4-m}$ and $C_5H_{4-n}$.

The heteroaromatic group preferably has a heteroaromatic ring and at least one substituent bonded to the ring. Concrete examples include heteroaromatic groups which have a furyl ring, a thienyl ring, a benzofuryl ring or a benzothienyl ring as the heteroaromatic ring, and a methyl group, an ethyl group, an n-butyl group, an isobutyl group, a t-butyl group, a phenyl group or a trimethylsilyl group as the substituent bonded to the ring. More preferably, the heteroaromatic group has a 2-furyl ring, a 2-thienyl ring, a 2-benzofuryl ring or a 2-benzothienyl ring as the heteroaromatic ring, and a methyl group, a t-butyl group, a phenyl group or a trimethylsilyl group as the substituent bonded to the ring. Concrete examples of the heteroaromatic group include a 2-(5-methyl)-furyl group, a 2-(5-t-butyl)-furyl group, a 2-(5-trimethylsilyl)-furyl group, a 2-(5-phenyl)-furyl group, a 2-(5-methyl)-thienyl group, a 2-(5-t-butyl)-thienyl group, a 2-(5-trimethylsilyl)-thienyl group, a 2-(5-phenyl)-thienyl group, a 2-(4,5-dimethyl)-furyl group, a 2-(4,5-dimethyl)-thienyl group, a 2-benzofuryl group and a 2-benzothienyl group.

In the metallocene compound of this invention, at least one substituent selected from the group consisting of substituents represented by $R^1_m$ and $R^2_n$, the substituent(s) bonded to the ring formed by the one pair of $R^1$'s, and the substituent(s) bonded to the ring formed by the one pair of $R^2$'s is the aforementioned heteroaromatic group which has a heteroaromatic ring and at least one substituent bonded to the ring.

Q represents a divalent group for cross-linking ($C_5H_{4-m}R^{1-m}_m$) and ($C_5H_{4-n}R^2_n$), and is a hydrocarbon group, an unsubstituted silylene group, hydrocarbon-substituted silylene group or a boron compound having a $R^3_2NB$ structure. $R^3$ represents a hydrocarbon group of 1–20 carbon atoms, a silicon-containing hydrocarbon group of 1–20 carbon atoms or a heteroaromatic group. Concrete examples of Q include a methylene group, an ethylene group, a dimethylsilylene group, a diphenylsilylene group, a dimethylamidoborane group, a diisopropylamidoborane group and a bis(trimethylsilane) amidoborane group. A dimethylsilylene group is preferable.

M represents a titanium atom, a zirconium atom or a hafnium atom, and preferable is a zirconium atom.

X and Y each independently represent a hydrogen atom, a halogen atom or a hydrocarbon group.

Preferably in the metallocene compound of this invention, n represents the integer of 3, one pair of $R^2$'s in the $C_5H_{4-n}R^2_n$ are bonded to each other to form at least one (monocyclic or polycyclic) ring, and the $R^2$ other than the pair of $R^2$'s is the aforementioned heteroaromatic group having a heteroaromatic ring and at least one substituent bonded to the ring. The preferred cyclic structure which is formed by the ring formed by one pair of $R^2$'s with $C_5H_{4-n}$ is an indenyl ring, tetrahydroindenyl ring, a benzoindenyl ring, a dihydroazulenyl ring or a cyclopentaphenanthrene ring. An indenyl ring, a benzoindenyl ring, and a dihydroazulenyl ring are particularly preferable.

Preferably in the metallocene compound of this invention, n represents the integer of 3, one pair of $R^2$'s in the $C_5H_{4-n}R^2_n$ are bonded to each other to form at least one ring, and the $R^2$ other than the aforementioned pair of $R^2$'s is bonded at the 2-position of the cyclopentadienyl ring $C_5H_{4-n}$. The preferred cyclic structure which the ring formed by one pair of $R^2$'s forms with $C_5H_{4-n}$ is an indenyl ring, tetrahydroindenyl ring, a benzoindenyl ring, a dihydroazulenyl ring or a cyclopentaphenanthrene ring. An indenyl ring, a benzoindenyl ring and a dihydroazulenyl ring are particularly preferable.

Particularly preferably in the metallocene compound of this invention, both n and m represent the integer of 3, respectively, one pair of $R^2$'s in the $C_5H_{4-n}R^2_n$ are bonded to each other to form at least one ring, one pair of $R^1$'s in the $C_5H_{4-m}R^2_m$ are also bonded to each other to form at least one ring, the $R^2$ other than the pair of $R^2$'s is bonded at the 2-position of the cyclopentadienyl ring $C_5H_{4-n}$, and the $R^1$ other than the pair of $R^1$'s is bonded at the 2-position of the cyclopentadienyl ring $C_5H_{4-m}$.

$R^1$ other than one pair of $R^1$'s and $R^2$ other than one pair of $R^2$'s are both preferably the aforementioned heteroaromatic group which has a heteroaromatic ring and at least one substituent bonded to the ring.

The metallocene compound of this invention preferably has a structure not having a plane of symmetry including M because of either the difference between $R^1$ and $R^2$ or the difference of the positions at which $R^1$ and $R^2$ are bonded to a cyclopentadienyl ring, or both.

Further in the metallocene compound of this invention, at least one substituent selected from the group consisting of substituents represented by $R^1_m$ and $R^2_n$, the substituent(s) bonded to the ring formed by the pair of $R^1$'s and the substituent(s) bonded to the ring formed by the pair of $R^2$'s is preferably a heteroaromatic group which has a heteroaromatic ring and a hydrocarbon group of 1–20 carbon atoms or silicon-containing hydrocarbon group of 1–20 carbon atoms bonded to the heteroaromatic ring, such as a 2-furyl ring, a 2-thienyl ring, a 2-benzofuryl ring or a 2-benzothienyl ring.

In the metallocene compound of this invention, at least one substituent selected from the group consisting of substituents represented by $R^1_m$ and $R^2_n$, the substituent(s) bonded to the ring formed by the aforementioned one pair of $R^1$'s and the substituent(s) bonded to the the ring formed by the aforementioned one pair of $R^2$'s is preferably a 2-(5-methyl)-furyl group, a 2-(5-t-butyl)-furyl group, a 2-(5-trimethylsilyl)-furyl group, a 2-(5-phenyl)-furyl group, a 2-(5-methyl)-thienyl group, a 2-(5-t-butyl)-thienyl group, a 2-(5-trimethylsilyl)-thienyl group, a 2-(5-phenyl)-thienyl group, a 2-(4,5-dimethyl)-furyl group, a 2-(4,5-dimethyl)-thienyl group, a 2-benzofuryl group or a 2-benzothienyl group.

Examples of the metallocene compound of this invention include, but are not limited to, dimethylsilylene bis(2-(2-(5-methyl)furyl)-indenyl) zirconium dichloride, dimethylsilylene bis(2-(2-(5-phenyl)-furyl)-indenyl) zirconium dichloride, dimethylsilylene bis(2-(2-(5-t-butyl)-furyl)-indenyl) zirconium dichloride, dimethylsilylene bis(2-(2-(5-trimethylsilyl)-furyl)-indenyl) zirconium dichloride, dimethylamidoborane bis(2-(2-(5-methyl)-furyl)-indenyl) zirconium dichloride, diisopropylamidoborane bis(2-(2-(5-methyl)-furyl)-indenyl) zirconium dichloride, bis(trimethylsilyl)amidoborane bis(2-(2-(5-methyl)-furyl)-indenyl) zirconium dichloride, dimethylsilylene bis(2-(2-(5-methyl)-thienyl)-indenyl) zirconium dichloride, dimethylsilylene bis-(2-(2-(5-phenyl)-thienyl)-indenyl) zirconium dichloride, dimethylsilylene bis(2-(2-(5-t-butyl)-thienyl)-indenyl) zirconium dichloride, dimethylsilylene bis (2-(2-(5-trimethylsilyl)-thienyl)-indenyl) zirconium dichloride, dimethylsilylene bis(2-(2-(5-methyl)-furyl)-4,5-benzoindenyl) zirconium dichloride, dimethylsilylene bis(2-(2-(5-phenyl)-furyl)-4,5-benzoindenyl) zirconium dichloride, dimethylsilylene bis(2-(2-(5-t-butyl)-furyl)-4,5-benzoindenyl) zirconium dichloride, dimethylsilylene bis(2-(2-(5-trimethylsilyl)-furyl)-4,5-benzoindenyl) zirconium dichloride, dimethylsilylene bis(2-(2-(5-methyl)thienyl)-4,5-benzoindenyl) zirconium dichloride, dimethylsilylene bis (2-(2-(5-phenyl)-thienyl)-4,5-benzoindenyl) zirconium dichloride, dimethylsilylene bis(2-(2-(5-t-butyl)-thienyl)-4,5-benzoindenyl) zirconium dichloride, dimethylsilylene bis (2-(2-(5-trimethylsilyl)-thienyl)-4,5-benzoindenyl) zirconium dichloride, dimethylsilylene bis(2-(2-(5-methyl)-furyl)-4-phenyl-indenyl) zirconium dichloride, dimethylsilylene bis(2-(2-(5-phenyl)-furyl)-4-phenyl-indenyl) zirconium dichloride, dimethylsilylene bis(2-(2-(5-t-butyl)-furyl)-4-phenyl-indenyl) zirconium dichloride, dimethylsilylene bis(2-(2-(5-trimethylsilyl)-furyl)-4-phenyl-indenyl) zirconium dichloride, dimethylsilylene bis (2-(2-(5-methyl)-thienyl)-4-phenyl-indenyl) zirconium dichloride, dimethylsilylene bis(2-(2-(5-phenyl)-thienyl)-4-phenyl-indenyl) zirconium dichloride, dimethylsilylene bis (2-(2-(5-t-butyl)-thienyl)-4-phenyl-indenyl) zirconium dichloride, dimethysilylene bis(2-(2-(5-trimethylsilyl)-thienyl)-4-phenyl-indenyl) zirconium dichloride, dimethylsilylene bis(2-(2-(5-methyl)-furyl)-4-phenyl-dihydroazulenyl) zirconium dichloride, dimethylsilylene bis (2-(2-(5-phenyl)-furyl)-4-phenyl-dihydroazulenyl) zirconium dichloride, dimethylsilylene bis(2-(2-(5-t-butyl)-furyl)-4-phenyl-dihydroazulenyl) zirconium dichloride, dimethylsilylene bis(2-(2-(5-trimethylsilyl)-furyl)-4-phenyl-dihydroazulenyl) zirconium dichloride, dimethylsilylene bis(2-(2-(5-methyl)-thienyl)-4-phenyl-dihydroazulenyl) zirconium dichloride, dimethylsilylene bis(2-(2-(5-phenyl)-thienyl)-4-phenyl-dihydroazulenyl) zirconium dichloride, dimethylsilylene bis(2-(2-(5-t-butyl)-thienyl)-4-phenyl-dihydroazulenyl) zirconium dichloride and dimethylsilylene bis(2-(2-(5-trimethylsilyl)-thienyl)-4-phenyl-dihydroazulenyl) zirconium dichloride.

Among the above metallocene compounds, preferable are dimethylsilylene bis(2-(2-(5-methyl)-furyl)-indenyl) zirconium dichloride, dimethylsilylene bis(2-(2-(5-t-butyl)-furyl)-indenyl) zirconium dichloride, dimethylsilylene bis(2-(2-(5-trimethylsilyl)-furyl)-indenyl) zirconium dichloride, dimethylsilylene bis(2-(2-(5-phenyl)-furyl)-indenyl) zirconium dichloride, dimethylsilene bis(2-(2-(5-methyl)thienyl)-indenyl) zirconium dichloride, dimethylsilylene bis(2-(2-(5-t-butyl)-thienyl)-indenyl) zirconium dichloride, dimethylsilylene bis(2-(2-(5-trimethylsilyl)-thienyl)-indenyl) zirconium dichloride, dimethylsilylene bis(2-(2-(5-phenyl)-thienyl)-indenyl) zirconium dichloride, dimethylsilylene bis(2-(2-(5-methyl)-furyl)-4-phenyl-indenyl) zirconium dichloride, dimethylsilylene bis(2-(2-(5-t-butyl)-furyl)-4-phenyl-indenyl) zirconium dichloride, dimethylsilylene bis(2-(2-(5-trimethylsilyl)-furyl)-4-phenyl-indenyl) zirconium dichloride, dimethylsilylene bis(2-(2-(5-phenyl)-furyl)-4-phenyl-indenyl) zirconium dichloride, dimethylsilylene bis(2-(2-(5-methyl)-thienyl)-4-phenyl-indenyl) zirconium dichloride, dimethylsilylene bis(2-(2-(5-t-butyl)-thienyl)-4-phenyl-indenyl) zirconium dichloride, dimethylsilylene bis(2-(2-(5-trimethylsilyl)-thienyl)-4-phenyl-indenyl) zirconium dichloride, dimethylsilylene bis(2-(2-(5-phenyl)-thienyl)-4-phenyl-indenyl) zirconium dichloride, dimethylsilylene bis(2-(2-(5-methyl)-furyl)-4,5-benzoindenyl) zirconium dichloride, dimethylsilylene bis(2-(2-(5-t-butyl)-furyl)-4,5-benzoindenyl) zirconium dichloride, dimethylsilylene bis(2-(2-(5-trimethylsilyl)-furyl)-4,5-benzoindenyl) zirconium dichloride, dimethylsilylene bis(2-(2-(5-phenyl)-furyl)-4,5-benzoindenyl) zirconium dichloride, dimethylsilylene bis(2-(2-(5-methyl)-thienyl)-4,5-benzoindenyl) zirconium dichloride, dimethylsilylene bis(2-(2-(5-t-buthyl)-thienyl)-4,5-benzoindenyl) zirconium dichloride, dimethylsilylene bis(2-(2-(5-trymethylsillyl)-thienyl)-4,5-benzoindenyl) zirconium dichloride, dimethylsilylene bis(2-(2-(5-phenyl)-thienyl)-4,5-benzoindenyl) zirconium dichloride, dimethylsilylene bis(2-(2-(5-methyl)-furyl)-4-phenyl-dihydroazulenyl) zirconium dichloride, dimethylsilylene bis(2-(2-(5-t-butyl)-furyl)-4-phenyl-dihydroazulenyl) zirconium dichloride, dimethylsilylene bis(2-(2-(5-trimethylsilyl)-furyl)-4-phenyl-dihydroazulenyl) zirconium dichloride, dimethylsilylene bis(2-(2-(5-phenyl)-furyl)-4-phenyl-dihydroazulenyl) zirconium dichloride, dimethylsilylene bis(2-(2-(5-methyl)-thienyl)-4-phenyl-dihydroazulenyl) zirconium dichloride, dimethylsilylene bis(2-(2-(5-t-butyl)-thienyl)-4-phenyl-dihydroazulenyl) zirconium dichloride, dimethylsilylene bis(2-(2-(5-trimethylsilyl)-thienyl)-4-phenyl-dihydroazulenyl) zirconium dichloride and dimethylsilylene bis(2-(2-(5-phenyl)-thienyl)-4-phenyl-dihydroazulenyl) zirconium dichloride.

The most preferable metallocene compounds are dimethylsilylene bis(2-(2-(5-methyl)-furyl)-indenyl) zirconium dichloride, dimethylsilylene bis(2-(2-(5-t-butyl)-furyl)-indenyl) zirconium dichloride, dimethylsilylene bis(2-(2-(5-trimethylsilyl)-furyl)-indenyl) zirconium dichloride, dimethylsilylene bis(2-(2-(5-phenyl)-furyl)-indenyl) zirconium dichloride, dimethylsilylene bis(2-(2-(5-methyl)-furyl)-4-phenyl-indenyl) zirconium dichloride, dimethylsilylene bis(2-(2-(5-t-butyl)-furyl)-4-phenyl-indenyl) zirconium dichloride, dimethylsilylene bis(2-(2-(5-trimethylsilyl)-furyl)-4-phenyl-indenyl) zirconium dichloride, dimethylsilylene bis(2-(2-(5-phenyl)-furyl)-4-phenyl-indenyl) zirconium dichloride, dimethylsilylene bis(2-(2-(5-methyl)-furyl)-4,5-benzoindenyl) zirconium dichloride, dimethylsilylene bis(2-(2-(5-t-butyl)-furyl)-4,5-benzoindenyl) zirconium dichloride, dimethylsilylene bis(2-(2-(5-trimethylsilyl)-furyl)-4,5-benzoindenyl) zirconium dichloride, dimethylsilylene bis(2-(2-(5-phenyl)-furyl)-4,5-benzoindenyl) zirconium dichloride, dimethylsilylene bis(2-(2-(5-methyl)-furyl)-4-phenyl-dihydroazulenyl) zirconium dichloride, dimethylsilylene bis(2-(2-(5-t-butyl)-furyl)-4-phenyl-dihydroazulenyl) zirconium dichloride, dimethylsilylene bis(2-(2-(5-trimethylsilyl)-furyl)-4-phenyl-dihydroazulenyl) zirconium dichloride and dimethylsilylene bis(2-(2-(5-phenyl)-furyl)-4-phenyl-dihydroazulenyl) zirconium dichloride.

The metallocene compounds of this invention are also characterized in that they can be synthesized in high yields by using relatively low-cost raw material.

Olefin Polymerization Catalyst

The olefin polymerization catalysts of this invention can be broadly divided into the following three types (1)–(3).

(1) The olefin polymerization catalyst (hereinafter referred to as "homogeneous metallocene catalyst" occasionally) comprising a metallocene compound mentioned above (hereinafter referred to as "component (A)" occasionally), an activating compound (hereinafter referred to as "component (B)" occasionally) and optionally an organoaluminum compound (hereinafter referred to as "component (D)" occasionally).

(2) The olefin polymerization catalyst comprising a supported metallocene catalyst (hereinafter referred to as "supported metallocene catalyst I" occasionally) produced from component (A), component (B), a support in the form of fine particles (hereinafter referred to as "component (C)" occasionally) and optionally component (D); and an organoaluminum compound (hereinafter referred to as "component (D')" occasionally).

(3) The olefin polymerization catalyst comprising a supported metallocene catalyst (hereinafter referred to as "supported metallocene catalyst II" occasionally) produced from component (A), a specific ion-exchangeable layer compound or an inorganic silicate (hereinafter referred to as "component (E)" occasionally) and optionally component (D); and component (D').

As component (B) mentioned above, an organoaluminum oxy compound or a compound which reacts with component (A) to form an ion pair is used.

As the organoaluminum oxy compound mentioned above, an aluminoxane represented by the following formula (2) or (3) can be used.

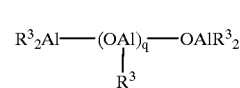

(2)

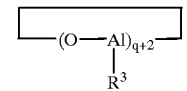

(3)

In the formulas, $R^3$ represents a hydrocarbon group of 1–6 carbon atoms. Concrete examples of this hydrocarbon group include alkyl groups such as a methyl group, an ethyl group, a propyl group, a butyl group, an isobutyl group, a pentyl group and a hexyl group; alkenyl groups such as an allyl group, a 2-methylallyl group, a propenyl group, an isopropenyl group, a 2-methyl-1-propneyl group and butenyl group; cycloalkyl groups such as a cyclopropyl group, a cyclobutyl group, a cyclopentyl group and a cyclohexyl group; and aryl groups. Hydrocarbon groups of 1–4 carbon atoms are preferable, and an alkyl group is particularly preferable. Each $R^3$ may be the same or different. q represents an integer in the range of 4–30, preferably 6–30, and particularly preferably 8–30.

The aluminoxane mentioned above can be prepared under various known conditions. Concrete examples of the method for the preparation are the following (a)–(f).

(a) A method of reacting a trialkyl aluminum with water in an organic solvent such as toluene and ether.

(b) A method of reacting a trialkyl aluminum with a salt which has crystallization water such as copper sulfate hydrate and aluminum sulfate hydrate.

(c) A method of reacting a trialkyl aluminum with the water absorbed on silica gel, etc.

(d) A method of reacting a mixture of trimethyl aluminum and triisobutyl aluminum with water in an organic solvent such as toluene and ether.

(e) A method of reacting a mixture of trimethyl aluminum and triisobutyl aluminum with a salt which has crystallization water such as copper sulfate hydrate and aluminum sulfate hydrate.

(f) A method which comprises reacting the water absorbed on silica gel, etc. with triisobutyl aluminum and subsequently reacting the product with trimethyl aluminum.

Concrete examples of the compound which reacts with component (A) to form an ion pair include a Lewis acid, an ionic compound, a borane compound and a carborane compound, which are reported in WO 88/05792 (EP 0277003 and JP-A-1-501950T), WO 88/05793 (EP 0277044 and JP-A-1-502036T), EP 0427697 (JP-A-3-179005), EP 0427696 (JP-A-3-179006), and EP 0426638 (JP-A-3-207704). The pertinent parts of the descriptions of the above literatures are incorporated herein by reference.

The Lewis acid preferably contains a boron atom. Non-exclusive concrete examples of the Lewis acid include trifluoroboron, triphenylboron, tris(4-fluorophenyl)boron, tris(3,5-fluorophenyl)boron, tris(4-fluoromethylphenyl)boron, tris(p-tolyl)boron, tris(o-tolyl)boron, tris(3,5-dimethylphenyl)boron and tris(pentafluorophenyl)boron. Tris(pentafluorophenyl)boron is particularly preferable.

The ionic compounds are salts of cationic and anionic compounds. An anion has an action to cationize the metallocene compound by reaction therewith and to stabilize the transition metal cation species by formation of an ion pair. The anions include those of organoboron compounds, organoarsenic compounds and organoaluminum compounds, and preferable are anions which are comparatively bulky and can stabilize the transition metal cation. The cations include metallic cations, organometallic cations, carbonium cations, tropium cations, oxonium cations, sulfonium cations, phosphonium cations and ammonium cations. Concrete examples of the cationic compound include triphenyl carbenium cation, tributyl ammonium cation, N,N-dimethylammonium cation and ferrocenium cation.

A salt containing a boron compound as an anionic compound can be preferably used as an ionic compound. Concrete examples of the trialkyl-substituted ammonium salt include triethylammonium tetra(phenyl)boron, tripropylammonium tetra(phenyl)boron, tri(n-butyl)ammonium tetra (phenyl) boron, trimethylammonium(p-tolyl)boron, trimethylammonium(o-tolyl)boron, tributylammonium tetra (pentafluorophenyl)boron, tripropylammonium tetra(o,p-dimethylphenyl)boron, tributylammonium tetra(m,m-dimethylphenyl)boron, tributylammonium tetra(p-trifluoromethylphenyl)boron, tri(n-butyl)ammonium tetra (o-tolyl)boron and tri(n-butyl)ammonium tetra(4-fluorophenyl)boron.

Concrete examples of the N-N-dialkylanilinium salt include N,N-dimethylanilinium tetra(phenyl)boron, N,N-diethylanilinium tetra(phenyl)boron and N,N,N-2,4,6-pentamethylanilinium(phenyl)boron. Concrete examples of the dialkylammonium salt include di(n-propyl)ammonium tetra(pentafluorophenyl)boron and dicyclohexylammonium tetra(pentafluorophenyl)boron. Concrete examples of the trialkylphosphonium salt and triarylphosphonium salt include trimethylphosphonium tetra(phenyl)boron, tri (methylphenyl)phosphonium tetra(phenyl)boron and tri (dimethylphenyl)phosphonium tetra(phenyl)boron.

The ionic compounds containing a boron atom used herein include triphenylcarbenium tetrakis (pentafluorophenyl)borate, N,N-dimethylanilinium tetrakis (pentafluorophenyl)borate, and ferrocenium tetra (pentafluorophenyl)borate, for example.

Among the above activating compounds, aluminoxane is particularly preferably used.

The component (D) optionally used in the aforementioned uniform metallocene catalyst I is represented by the formula: $AlR^4_s R^5_t X_{3-(s+t)}$.

In the formula, $R^4$ and $R^5$ each independently represent a hydrocarbon group such as an alkyl group of 1–10 carbon atoms, a cycloalkyl group of 1–10 carbon atoms and an aryl group of 1–10 carbon atoms, and a phenyl group optionally having a substituent such as an alkoxy group, a fluorine atom, a methyl group and a trifluorophenyl group, X represents a halogen atom, and s and t represent any one of integers satisfying the expression:

$$0 < s+t \leq 3.$$

Concrete examples of the component (D) represented by the aforementioned formula include trialkyl aluminums such as trimethyl aluminum, triethyl aluminum, triisopropyl aluminum, triisobutyl aluminum, tri-n-butyl aluminum, tri-n-hexyl aluminum and tri-n-octyl aluminum; dialkyl aluminum halides such as dimethyl aluminum chloride, dimethyl aluminum bromide, diethyl aluminum chloride and diisopropyl aluminum chloride; alkyl aluminum sesquihalides such as methyl aluminium sesquichloride, ethyl aluminium sesquichloride, ethyl aluminium sesquibromide and isopropyl aluminum sesquichloride; and mixtures of two or more components (D). Trialkyl aluminum is particularly preferable.

The component (C) used for producing the supported metallocene catalyst I of this invention is an inorganic support or an organic support. An inorganic or organic support preferably used is in the form of fine granular or spherical solid particles having a diameter in the range of 1–500 μm, preferably in the range of 5–300 μm, and more preferably in the range of 10–150 μm.

The finely particulate inorganic support has a specific surface area in the range of 50–1,000 $m^2$/g, preferably in the range of 100–700 $m^2$/g, and a pore volume in the range of 0.3–2.5 $m^3$/g.

The finely particulate inorganic supports include $SiO_2$, $Al_2O_3$, MgO, $TiO_2$, ZnO, mixtures thereof, and complex oxides thereof, for example. The supports containing $SiO_2$ or $Al_2O_3$ as main components are particularly preferable. Concrete examples of the inorganic compound include $SiO_2$, $Al_2O_3$, MgO, $SiO_2$—$Al_2O_3$, $SiO_2$—MgO, $SiO_2$—$TiO_2$ and $SiO_2$—$Al_2O_3$—MgO. $SiO_2$ is particularly preferable.

The finely particulate inorganic support mentioned above is generally calcined at a temperature of 100–1,000° C., preferably 300–900° C., and particularly preferably 400–900° C. prior to use. The amount of water adsorbed on the surface of the finely particulate inorganic support after calcined it not more than 0.1% by weight, preferably not more than 0.01% by weight and the content of a hydroxyl group on the surface of the support is not less than 1.0% by weight, preferably in the range of 1.5–4.0% by weight, and more preferably in the range of 2.0–3.5% by weight. These finely particulate inorganic supports may be subjected to a contact treatment with an organoaluminum compound and/or a halogen-containing silicone compound, prior to the use.

The finely particulate organic supports include finely particulate organic polymers such as finely particulate polymers of polyolefins, for example, polyethylene, polypropylene, poly-1-butene and poly-4-methyl-1-pentene, and those of polystyrenes.

Concrete examples of the component (E) used in the production of the aforementioned supported metallocene catalyst II include ion-exchangeable layer compounds and inorganic silicates. The term "ion-exchangeable layer" used herein does not include silicates.

The aforementioned ion exchangeable layer compounds as the component (E) include ionic crystalline compounds of a hexagonal closest packing type, an antimony type, a $CdCl_2$ type and a $CdI_2$ type, which have a layer crystal structure. Specific examples of the ion exchangeable layer compounds may include crystalline acid salts of polyvalent metals such as $\alpha$-$Zr(HAsO_4)_2 \cdot H_2O$, $\alpha$-$Zr(HPO_4)_2$, $\alpha$-$Zr(KPO_4)_2 \cdot 3H_2O$, $\alpha$-$Ti(HPO_4)_2$, $\alpha$-$Ti(HAsO_4)_2 \cdot H_2O$, $\alpha$-$Sn(HPO_4)_2 \cdot H_2O$, $\gamma$-$Zr(HPO_4)_2$, $\gamma$-$Ti(HPO_4)_2$ and $\gamma$-$Ti(NH_4PO_4)_2 \cdot H_2O$.

The aforementioned ion exchangeable layer compounds may be treated with salts and/or acids, if necessary. The ion exchangeable layer compounds except for silicates without any treatment with salts or acids have such a crystal structure that layers formed by ionic bonds, etc. are overlapped in parallel to one another with a weak bonding force therebetween, and therefore, the layers contain exchangeable ions.

The aforementioned inorganic silicates as the component (E) include clays, clay minerals, zeolite and diatomaceous earth. These inorganic silicates may be either synthetic products or natural minerals. Specific examples of clays or clay minerals may include allophane group such as allophane; kaolin group such as dickite, nacrite, kaolinite and anauxite; halloysite group such as meta-halloysite and halloysite; serpentine group such as chrysotile, lizardite and antigorite; smectite group such as montmorillonite, sauconite, beidellite, nontronite, saponite and hectorite; vermiculite minerals such as vermiculite; mica minerals such as illite, sericite and glauconite; attapulgite; sepiolite; palygorskite; bentonite; gnarl clay; gairome clay; hisingerite; pyrophyllite; and chlorite groups. These inorganic silicates may be in the form of mixed layers. In addition, the synthetic inorganic silicates include synthetic mica, synthetic hectorite, synthetic saponite and synthetic taeniolite.

Among the above inorganic silicates, preferable are kaolin group, halloysite group, serpentine group, smectite group, vermiculite minerals, mica minerals, synthetic mica, synthetic hectorite, synthetic saponite and synthetic taeniolite. Particularly preferred inorganic silicates are smectite, vermiculite minerals, synthetic mica, synthetic hectorite, synthetic saponite and synthetic taeniolite. These inorganic silicates may be used without any treatment or after treatments such as crushing by a ball mill and screening. Further, they may be used singly or in combination of the two or more.

The aforementioned ion exchangeable layer compounds and the inorganic silicates can be treated with salts and/or acids to control an acid strength of these solid compounds. Further, when these compounds are treated with salts, ion composites, molecular composites or organic derivatives are formed so as to appropriately change the surface area and the interlayer distance. Specifically, exchangeable ions existing between the respective layers can be replaced with other bulkier ions by the aid of ion exchanging properties of these compounds, thereby obtaining a layer substance having an increased interlayer distance.

Though the component (E) may be used without any pretreatment, it is preferred that metal cations contained therein are ion-exchanged with cations dissociated from the salts and/or acids mentioned below.

The salts used for the ion exchange may be compounds comprising a cation which contains at least one atom selected from the group consisting of Group 1–14 atoms; preferably compounds comprising a cation which contains at least one atom selected from the group consisting of Group 1–14 atoms and at least one anion derived from an atom or atomic group selected from the group consisting of halogen atoms, inorganic acids and organic acids; more preferably compounds comprising a cation which contains at least one atom selected from the group consisting of Group 2–14 atoms and at least one anion selected from the group consisting of Cl, Br, I, F, $PO_4$, $SO_4$, $NO_3$, $CO_3$, $C_2O_4$, $ClO_4$, $OOCCH_3$, $CH_3COCHCOCH_3$, $OCl_2$, $O(NO_3)_2$, $O(ClO_4)_2$, $O(SO_4)$, OH, $O_2Cl_2$, $OCl_3$, OOCH and $OOCCH_2CH_3$. These salts may be used singly or in combination of the two or more.

The acids used for the ion exchange may be selected from hydrochloric acid, sulfuric acid, nitric acid, acetic acid and oxalic acid. These acids may be used singly or in combination of the two or more. The salt treatment can be used in combination with the acid treatment. The methods in which the salt treatment and the acid treatment are combined include a method of conducting the acid treatment after the salt treatment, a method of conducting the salt treatment after the acid treatment, a method of conducting the salt and acid treatments simultaneously, and a method of conducting the salt and acid treatments simultaneously after the salt treatment. The acid treatment has such effects, in addition to aforementioned ion exchange, that impurities can be removed from the surface of the component (E), and that a part of cations contained in the crystal structure such as Al, Fe, Mg and Li can be eluted therefrom.

The conditions for the salt or acid treatment are not particularly limited. Usually, the concentration of the salt or acid is in the range of 0.1 to 30% by weight; the treating temperature is from room temperature to a boiling point of the solvent used; and the treating time is from 5 minutes to 24 hours. Such conditions are preferably selected so that at least a part of the compound to be treated is solved out. The salts and the acids are usually used in the form of an aqueous solution.

In the aforementioned salt and/or acid treatments, the component (E) may be pulverized or granulated before, during or after the salt and/or acid treatments to adjust the shape thereof. In addition, other chemical treatments such as alkali treatment or organometallics treatment may be used in combination. The component (E) thus prepared preferably has a pore volume of not less than 0.1 cc/g, more preferably 0.3 to 5 cc/g, as measured with respect to pores having a radius of not less than 20 Å by a mercury-penetrating method. The component (E) prepared in water solution generally contains adsorbed water or interlayer water. Herein, the adsorbed water means water adsorbed on a surface or a crystal fracture face of the ion exchangeable layer compound or the inorganic silicate, and the interlayer water means water existing between the crystal layers.

In accordance with the present invention, it is preferred that the component (E) is used after removal of the aforementioned adsorbed water or interlayer water. The methods for removing the water are not particularly limited, but may include dehydrating methods such as heating under a flowing gas and heating under reduced pressure, and azeotropic dehydration with an organic solvent. The heating may be conducted at such a temperature that no adsorbed water and interlayer water exists in the component (E). The heating temperature is usually not lower than 100° C., preferably not lower than 150° C. However, such a high temperature that causes destruction of the crystal structure should be avoided. The heating time is usually not less than 0.5 hour, preferably not less than one hour. The weight loss of the component (E) thus treated is preferably not more than 3% by weight as determined by heating at a temperature of 200° C. for 2 hours under a vacuum condition of 1 mmHg.

In accordance with the present invention, in the case of using the component (E) whose weight loss is adjusted to not more than 3% by weight based on the weight of the component (E), it is preferred that the weight loss of the component (E) is maintained also when the component (E) is brought into contact with the essential component (A) and the optional component (D).

Now, the method for producing the supported metallocene catalysts I and II will be described below.

The supported metallocene catalyst I is obtained by reacting the component (A) with the component (B) and optionally the component (D) in the presence of the component (C). The order of adding the components (A) and (B) to the component (C) may be changed arbitrarily. For example, the component (A) dissolved in a proper hydrocarbon solvent is first added to the component (C) and thereafter the component (B) is added thereto. The components (B) and (A) which reacted in advance may be simultaneously added to the component (C). Alternatively, the component (B) is first added to the component (C) and thereafter the component (A) is added thereto. The temperature of the reaction is generally in the range of −20 to 200° C. and preferably in the range of 0 to 120° C. The time required for the reaction is generally not less than 0.1 minute, preferably in the range of one minute to 200 minutes. The supported metallocene catalyst obtained as described above is used after prepolymerized with a small amount of an olefin, if necessary.

Concrete examples of the olefin to be used for the prepolymerization include ethylene, propylene, 1-butene, 1-hexene, 3-methyl-1-butene and 4-methyl-1-pentene. These olefins may be used in combination of the two or more.

The supported metallocene catalyst I preferably used in the production of the olefin polymer of this invention is a supported metallocene catalyst prepared by sequentially performing the following step (a)–step (c) or a preactivated supported metallocene catalyst obtained by sequentially performing the following step (a)–step (d), for example.

(a) The step of preparing a metallocene catalyst by reacting a metallocene compound (A) with an aluminoxane in an inert solvent;

(b) The step of preparing a crude supported metallocene catalyst by bringing the metallocene catalyst obtained in the step (a) into contact with a finely particulate inorganic support in the presence of an inert solvent at a temperature of 85–150° C., and thereby depositing the metallocene catalyst on the finely particulate inorganic support;

(c) The step of preparing a purified supported metallocene catalyst by washing the slurry containing the crude supported metallocene catalyst obtained in the step (b) at least twice with an aliphatic hydrocarbon at a temperature of −50 to 50° C.; and (d) The step of preparing a preactivated supported metallocene catalyst by bringing the supported metallocene catalyst obtained in the step (c) into contact with an olefin, thereby prepolymerizing the olefin, and further depositing 0.01–100 kg of an olefin prepolymer per 1 kg of the supported metallocene catalyst on the catalyst.

In the step (a), 10–1,000 mol, preferably 20–500 mol of aluminoxane in terms of aluminum atom per mol of the metallocene compound (A) is reacted with the compound (A) in an inert solvent at a temperature of −50 to 100° C., preferably 0 to 50° C., for 1 minute to 10 hours, preferably 3 minutes to 5 hours to form a metallocene catalyst.

The use of the inert solvent is favorable for the purpose of carrying out the uniform and efficient reaction. The amount of the inert solvent used is not particularly limited, and it is generally in the range of 10–10,000 liters, preferably in the range of 10–1,000 liters, per mol of the metallocene compound (A).

Concrete examples of the inert solvent used in the aforementioned reaction include aromatic hydrocarbons such as benzene, toluene, xylene and cumene; aliphatic hydrocarbons such as butane, tetramethyl butane, pentane, ethyl pentane, trimethyl pentane, hexane, methyl hexane, ethyl hexane, dimethyl hexane, heptane, methyl heptane, octan, nonane, decane, hexadecane and octadecane; alicyclic hydrocarbons such as cyclopentane, methylcyclopentane, cyclohexane and cyclooctane; halogenated hydrocarbons obtained by substituting halogens for the aforementioned aromatic hydrocarbons, aliphatic hydrocarbons and alicyclic hydrocarbons; and mixed solvents thereof.

Ethers such as ethyl ether and tetrahydrofuran can be also used. The preferred inert solvents are aromatic hydrocarbons. The solvent of a commercially available aluminoxane solution may be used for the reaction as it is or in combination with other aromatic hydrocarbons, for example.

In the step (b) subsequent to the step (a), the crude supported metallocene catalyst is obtained in the form of a solid product having the metallocene catalyst mentioned above deposited on the finely particulate inorganic support by bringing the metallocene catalyst obtained in the step (a) into contact with the finely particulate inorganic support in the presence of the inert solvent used as the reaction solvent in the step (a) at a temperature of 85–150° C. In this contact reaction, an inert solvent may be used additionally, if necessary.

Regarding the content ratio of the metallocene catalyst to the finely particulate inorganic support in the crude supported metallocene catalyst, the amount of the finely particulate inorganic support is in the range of 1–1,000 kg, preferably in the range of 5–500 kg, per mol of the transition metal atom originating in the metallocene compound (A) contained in the reaction product of the metallocene compound (A) as the metallocene catalyst and the aluminoxane.

The amount of the inert solvent used in the step (b) is in the range of 10–10,000 liters, preferably in the range of 10–1,000 liters, per mol of the transition metal atom originating in the metallocene compound (A) contained in the reaction product of the metallocene compound (A) as the metallocene catalyst and the aluminoxane.

The contact between the metallocene catalyst and the finely particulate inorganic support is carried out at a temperature of 85–150° C., preferably 90–130° C., and particularly preferably 95–120° C. for 5 minutes to 100 hours, preferably 10 minutes to 50 hours. The temperature condition is a particularly important factor. When this contact is carried out at a temperature in the above-described range, the resultant supported metallocene catalyst can have a high polymerization activity. When this catalyst is used for the polymerization of an olefin, the resultant olefin polymer can have a high bulk specific gravity and a good powder morphology.

In the subsequent step (c), the purified supported metallocene catalyst is obtained by washing the crude supported metallocene catalyst obtained in the step (b) which contains the inert solvent at least twice with an aliphatic hydrocarbon at a temperature of −50 to 50° C.

Concrete examples of the aliphatic hydrocarbon used for the washing include the aliphatic hydrocarbons and their mixtures mentioned above as the inert solvent. n-Hexane, isopentane, and mixtures thereof are preferable.

The washing in the step (c) may comprise separating the inert solvent by filtration, centrifugation, or decantation from the slurry formed of the inert solvent and the crude supported metallocene catalyst after the step (b) and thereafter washing the crude supported metallocene catalyst with an aliphatic hydrocarbon. Alternatively, it may comprise adding an aliphatic hydrocarbon without separating the inert solvent from the slurry formed of the inert solvent and the crude metallocene catalyst after the step (b), separating the mixed solvent of the inert solvent and the aliphatic hydrocarbon in the same manner as described above, and thereafter washing the crude supported metallocene catalyst by the use of the aliphatic hydrocarbon. For the washing in the step (c), the latter method is particularly preferable.

The aforementioned washing is carried out repeatedly till the liquation of the metallocene catalyst into the aliphatic hydrocarbon ceases, by using 1–500 liters, preferably 10–100 liters of the aliphatic hydrocarbon per kg of the finely particulate inorganic support used in the step (b) at a temperature of −50 to 50° C., preferably −30 to 40° C., and particularly preferably −30 to 30° C. in each washing.

Though the washing is preferably carried out at least twice, and generally not less than four times, the number of washings is not limited thereto.

The temperature of the washing is an important factor. When the washing is carried out at a temperature in the above-described range, the resultant supported metallocene catalyst has a high polymerization activity. When the polymerization of an olefin is carried out by the use of this catalyst, the resultant olefin polymer can have a particularly high bulk specific gravity and a good powder morphology.

The preactivated supported metallocene catalyst used in this invention is obtained in the step (d) as described above by bringing the supported metallocene catalyst obtained in the step (c) into contact with an olefin, thereby prepolymerizing the olefin and depositing 0.01–100 kg of the olefin prepolymer per kg of the supported metallocene catalyst on the catalyst.

The olefin prepolymer to be deposited on the preactivated supported metallocene catalyst is an olefin of 2–20 carbon atoms. Concrete examples of the olefin include homopolymers of ethylene, propylene, 1-butene, 1-pentene, 4-methyl-1-pentene, 2-methyl-1-pentene, 1-hexene, 1-octene, 1-decene and 1-dodecene, and copolymers formed by combining two or more such olefins. Ethylene homopolymer, propylene homopolymer, ethylene/olefin copolymers formed of ethylene and olefin other than ethylene, and propylene/olefin copolymers formed of propylene and an olefin other than propylene are particularly preferable. Further, the olefin prepolymer preferably has an intrinsic viscosity [η] of 0.1–10 dl/g, preferably 0.2–7 dl/g, as determined in decalin at 135° C.

The olefin is preferably prepolymerized by a method which comprises introducing the olefin into the slurry of the supported metallocene catalyst obtained in the step (c) dispersed in an aliphatic hydrocarbon, thereby bringing the olefin into contact with the supported metallocene catalyst and prepolymerizing the olefin. As the slurry of the supported metallocene catalyst dispersed in the aliphatic hydrocarbon, the catalyst obtained by the washing at the final stage of the step (c) may be used without separated from the aliphatic hydrocarbon. Alternatively, the catalyst may be separated from the aliphatic hydrocarbon and subsequently redispersed in the aliphatic hydrocarbon of the same kind and then put to use.

Though the prepolymerization of the olefin may be carried out in a liquid phase using the olefin itself to be polymerized as a solvent or in a gas phase without any solvent, it is preferably carried out in the presence of an aliphatic hydrocarbon for the controlled polymerization of a small amount of olefin and the uniform prepolymerization.

The prepolymerization of the olefin in the aliphatic hydrocarbon is carried out by introducing 0.01–1,000 kg, preferably 0.1–500 kg of the olefin into the slurry formed of 0.005–5 $m^3$, preferably 0.01–1 $m^3$ of the aliphatic hydrocarbon per kg of the supported metallocene catalyst, thereby bringing the olefin into contact with the aliphatic hydrocarbon at a temperature of −50 to 100° C., preferably 0–50° C. for 1 minute to 50 hours, preferably 3 minutes to 20 hours.

In the prepolymerization of the olefin mentioned above, the reaction product of the metallocene compound (A) and the aluminoxane preferably used as the activating compound (B) is deposited on the supported metallocene catalyst, and there is no need to add a co-catalyst such as an organoaluminum compound, for example, trialkyl aluminum and aluminoxane. However, a co-catalyst may be added, if necessary. The amount of the co-catalyst added is not more than 1,000 mols, preferably not more than 500 mols, in terms of aluminum atom, per mol of the transition metal atom originating in the metallocene compound (A) in the supported metallocene catalyst.

In this invention, the prepolymerization of the olefin is preferably carried out in the presence of hydrogen so that the weight average molecular weight (Mw) of the resultant olefin prepolymer is in the range of 100,000–500,000 g/mol.

The supported metallocene catalyst II used in this invention is prepared by bringing the components (A), (E) and (D) into contact with each other. Though the method of this contact is not particularly limited, the following methods are available.

(1) Method of bringing the components (A) and (E) into contact with each other;

(2) Method of bringing the components (A) and (E) into contact with each other and then adding the component (D) to the mixture;

(3) Method of bringing the components (A) and (D) into contact with each other and then adding the component (E) to the mixture;

(4) Method of bringing the components (E) and (D) into contact with each other and then adding the component (A) to the mixture; and (5) Method of bringing the components (A), (E) and (D) into contact with each other at the same time.

The contact between these components may be performed not only upon the production of the catalyst but also upon prepolymerization or polymerization of the olefins.

During or after the respective components are brought into contact with each other, polymers such as polyethylene and polypropylene or solid components of inorganic oxides such as silica and alumina may co-exist therein or may be contacted therewith.

The contact between the respective components can be conducted in an atmosphere of an inert gas such as nitrogen or in the presence of inert hydrocarbon solvent such as pentane, hexane, heptane, toluene and xylene. Further, the contact is preferably conducted at a temperature of from −20° C. to a boiling point of the solvent used, more preferably from room temperature to the boiling point of the solvent used.

The amount of the component (A) used is usually in the range of $10^{-4}$ to 10 mmol, preferably $10^{-3}$ to 5 mmol per gram of the component (E). The amount of the component (D) used is usually in the range of 0.01 to $10^4$ mmol, preferably 0.1 to 100 mmol per gram of the component (E). In addition, the atomic ratio of the transition metal contained in the component (A) to aluminum contained in the component (D) is usually in the range of 1/0.01 to $1/10^6$, preferably 1/0.1 to $1/10^5$. The catalyst thus prepared may be used as it is without washing, or may be used after washing. Further, the catalyst can be used in combination with additional component (D), if required. Specifically, when the components (A) and/or (E) and the component (D) are used to prepare the catalyst, the additional component (D) may be added to a reaction system separately from the preparation of the catalyst. In this case, the amount of the component (D) added can be selected so that the atomic ratio of the transition metal contained in the component (A) to aluminum contained in the component (D) is in the range of 1/0 to $1/10^4$, preferably 1/1 to $1/10^3$.

Further, in the case of the supported metallocene catalyst II prepared as described above, the olefin is prepolymerized to deposit the olefin prepolymer on the supported catalyst and then used for the production of the olefin polymer of this invention, in the same manner as the case of the supported metallocene catalyst I.

The supported metallocene catalyst I or II thus obtained is further combined with an organoaluminum compound (component (D')) to produce the olefin polymerization catalyst, which is advantageously used for the production of the olefin polymer of this invention.

The component (D') used in combination with the supported metallocene catalyst I or II in the production of the olefin polymer is selected from the aforementioned organoaluminum compounds which are useful for the production of the supported metallocene catalyst I or II. However, it can be the other organoaluminum compounds.

The amount of the component (D') to be used in the production of the olefin polymer is selected so that the amount of the Al atom in the component (D') is in the range of 1–5,000 mols, preferably in the range of 5–3,000 mols, and particularly preferably in the range of 10–1,000 mols per mol of the transition metal atom originating in the metallocene compound (A) contained in the supported metallocene catalyst or the preactivating supported metallocene catalyst.

The amount of the supported metallocene catalyst or the preactivated supported metallocene catalyst used for polymerization is in the range of $1 \times 10^{-10}$ to $1 \times 10^{-3}$ mol, preferably in the range of $1 \times 10^{-9}$ to $1 \times 10^{-4}$ mol in terms of the transition metal atom originating in the metallocene compound (A) contained per liter of the polymerization volume. The above-described amount of the catalyst makes it possible to efficiently polymerize the olefin at a controlled velocity of polymerization reaction.

The term "polymerization volume" as used herein means the volume of the liquid phase in the polymerization vessel in the case of the liquid phase polymerization or the volume of the gas phase in the polymerization vessel in the case of the gas phase polymerization.

Method for Production of Olefin Polymer

In this invention, the term "olefin" refers to an olefin of 2–20 carbon atoms. Concrete examples of the olefin include ethylene, propylene, 1-butene, 1-pentene, 1-hexene, 1-heptene, 1-octene, 1-decene, 1-dodecene, 1-hexadecene, 4-methyl-1-pentene, and mixtures of two or more such olefins. These olefins may be copolymerized with styrene, vinyl cyclohexane, diene, etc. Styrene is preferably copolymerized with ethylene.

The most preferably used olefin in this invention is propylene or a mixture of propylene with at least one olefin other than propylene. The most preferred olefin other than propylene is ethylene or a mixture of ethylene with 1-butene.

The term "olefin polymer" as used in this invention means the homopolymer of an olefin or the copolymer of two or more olefins.

The olefin polymer to be produced by using the olefin polymerization catalyst of this invention is preferably the homopolymer of propylene or the propylene/olefin copolymer of propylene and an olefin other than propylene containing not less than 50% by weight of the propylene unit based on the weight of the copolymer. The propylene/olefin copolymer may be a random copolymer, a block copolymer or a random block copolymer.

The olefin polymer to be produced by using the olefin polymerization catalyst of this invention particularly has the stereoregularity controlled to a very high degree.

Specifically, the proportion of the number of moles of the propylene unit originating from 2,1-insertion of the propylene monomer and the proportion of the number of moles of the propylene unit originating from 1,3-insertion of the propylene monomer are each independently not more than 2 mol %, preferably not more than 1 mol %, and particularly preferably not more than 0.5 mol %, based on the total number of moles of the propylene unit forming the olefin polymer. Particularly, this invention is characterized in that the optimum selection of the condition for production of the catalyst and/or the olefin polymer of this invention produces the olefin polymer wherein the proportion of the number of moles of the propylene unit originating from 2,1-insertion of the propylene monomer and the proportion of the number of moles of the propylene unit originating from 1,3-insertion of the propylene monomer are each independently controlled to not more than 0.05 mol %, preferably not more than 0.04 mol %, and particularly preferably not more than 0.02 mol %, based on the total number of moles of the propylene unit forming the olefin polymer.

Though the isotactic pentad ratio ($I_5$) of the produced olefin polymer is not particularly limited, it is properly in the range of 0.400–0.990, preferably in the range of 0.800–0.960, more preferably in the range of 0.820–0.960, and particularly preferably in the range of 0.840–0.930.

The olefin polymer, particularly the propylene polymer, to be produced according to this invention is also characterized by satisfying the following relational expression (4) between the melting point (Tm) determined by use of a differential scanning calorimeter (DSC) and the isotactic pentad ratio ($I_5$):

$$Tm < 142.1 \times I_5 + 22.0 \quad (4)$$

The olefin polymer, particularly the propylene polymer, to be produced by using the olefin polymerization catalyst of this invention has the isotactic triad ratio ($I_3$) of the propylene unit chain part formed of head-tail bond in the range of 0.50–0.99, preferably in the range of 0.60–0.98, more preferably in the range of 0.80–0.98, and particularly preferably in the range of 0.85–0.94 as determined by the $^{13}$C-NMR.

The proportion of the number of moles of the propylene unit originating from 2,1-insertion of the propylene monomer and that of the number of moles of the propylene unit originating from 1,3-insertion of the propylene monomer based on the total number of moles of the propylene unit forming the olefin polymer, the isotactic pentad ratio ($I_5$), and the isotactic triad ratio ($I_3$) are determined by the $^{13}$C-nuclear magnetic resonance spectrum in accordance with the method shown below.

Specifically, a test sample (olefin polymer) is dissolved in a mixed solution of o-dichlorobenzene/benzene bromide at a weight ratio of 8/2 so that the concentration thereof in the solution should be 20% by weight. The test solution thus obtained is analyzed by the $^{13}$C-nuclear magnetic resonance spectrum using a wavelength of 67.20 MHz and a temperature of 130° C. "JEOL-GX270NMR (trade name)" manufactured by Japan Electron Optics Laboratory Co., Ltd. may be used as the apparatus for this analysis.

In the case of the honiopolymer of propylene, the "isotactic pentad ratio ($I_5$)" and the "isotactic triad ratio ($I_3$)" are indices designating the stereoregularity of a polymer, which are determined by the $^{13}$C-nuclear magnetic resonance spectrum proposed by A. Zambelli et al. In "Macromolecules, 6, 925 (1973)". The peaks appearing in the $^{13}$C-nuclear magnetic resonance spectrum are assigned by the method of A. Zambelli et al, Macromolecules, 8 687 (1975). The related parts of descriptions in the above literatures are incorporated herein by reference.

The isotactic triad ratio ($I_3$) of the copolymer is calculated based on the method proposed in JP-A-7-149833 and JP-A-8-283343.

Specifically, the term "isotactic pentad ratio ($I_5$)" expresses the proportion of the five propylene units continuously linked in the meso form to the total number of propylene units forming the olefin polymer. The term "isotactic triad ratio ($I_3$) expresses the proportion of three propylene units continuously linked in the meso form to the total number of propylene units in the molecular chain of the olefin polymer. The higher isotactic pentad ratio ($I_5$) and the higher isotactic triad ratio ($I_3$) indicate the higher isotacticity of the test sample.

The isotactic pentad ratio ($I_5$) is particularly used as the index of the isotacticity of a homopolymer and the isotactic triad ratio ($I_3$) as the index of the isotacticity of a homopolymer and a copolymer.

The proportion of the number of moles of the propylene unit originating from 2,1-insertion of the propylene monomer and that of the number of moles of the propylene unit originating from 1,3-insertion of the propylene monomer based on the total number of moles of the propylene unit forming the olefin polymer are indices indicating the stereoregularity of the olefin polymer including the propylene units determined by the $^{13}$C-nuclear magnetic resonance spectrum, based on the method published by Tsutsui et al. in "Polymer, 30, 1350 (1989)". The related parts of descriptions in these literatures are incorporated herein by reference.

The melting point (Tm) is determined by a DSC-7 differential scanning calorimeter manufactured by Perkin Elmer Inc. First, the polymer as the test sample is heated to elevate the temperature thereof from room temperature to 230° C. at a rate of 30° C./min., retained at that temperature for 10 minutes, then cooled to −20° C. at a rate of −20° C/min., and then retained at that temperature for 10 minutes. Thereafter, it is heated again at a rate of 20° C./min to find the temperature which shows a peak of melting of the polymer. This temperature is reported as the melting point.

The olefin polymer obtained by using the metallocene compound of this invention has a weight average molecular weight (Mw) preferably in the range of $5 \times 10^4$ to $5 \times 10^5$ g/mol, and more preferably in the range of $1 \times 10^5$ to $5 \times 10^5$ g/mol. The ratio of the weight average molecular weight (Mw) to the number average molecular weight (Mn), i.e., (Mw/Mn) is preferably in the range of 1.5–3.8, more preferably in the range of 1.5–3.5, and most preferably in the range of 1.8–2.5.

The olefin polymer obtained by using the metallocene compound of this invention has a melt flow rate (based on JIS K7210 and determined under the condition 14 shown in Table 1) preferably in the range of 0.5–300 g/10 min, and more preferably in the range of 0.5–100 g/10 min. If the melt flow rate is lower than 0.5 g/10 min or higher than 300 g/10 min, the olefin polymer will have difficulty in molding by a known molding machine.

The process for producing the olefin polymer in this invention may be any one of the known processes. The method of slurry polymerization which polymerizes olefins in inert solvents, for example, aliphatic hydrocarbons such as butane, pentane, hexane, heptane and isooctane; alicyclic hydrocarbons such as cyclopentane, cyclohexane and methylsiclohexane; aromatic hydrocarbons such as toluene, xylene and ethylbenzene; gasoline fractions, and hydrogenated diesel oil fractions may be adopted. Further, the method of bulk polymerization which uses olefins themselves as solvents and the method of gas phase polymerization which implements the polymerization of an olefin in a gas phase may be adopted. A combination of two or more of such polymerization processes can also be adopted. The most preferable combination is a combination of the first stage by the method of bulk polymerization with the subsequent second stage by the method of gas phase polymerization. Further, the method of solution polymerization can be used.

The olefin polymer of this invention is produced at a polymerization temperature of −50 to 150° C., preferably 20 to 120° C., and more preferably 40 to 100° C. under a polymerization pressure of atmospheric pressure to 9.9 MPa (gauge), and preferably 0.4 to 5.0 MPa (gauge). The produced olefin polymer may have the molecular weight adjusted, if necessary, by introducing such a chain transfer agent as hydrogen.

After the polymerization reaction, the olefin polymer is obtained by separating the unreacted monomer and hydrogen from the polymerization system and treating this system to inactivate the catalyst.

The olefin polymer obtained by the method of production of this invention may be incorporated therein with various additives such as antioxidant, ultraviolet absorber, antistatic agent, nucleating agent, lubricant, flame retardant, antiblocking agent, coloring agent, and inorganic or organic filler, and further, various synthetic resins, if necessary, then generally melted and kneaded with a melt-mixing device at a temperature of 190–350° C. for 20 seconds to 30 minutes, extruded into strands as required, and further pelletized.

Thus, it is used in the form of pellets for the production of various molded articles.

The olefin polymer thus obtained by this invention can be suitably used for films, sheets, fibers, infection molded products, blow molded products, containers, stretched yarns, non-woven fabrics, foam, etc., but is not limited thereto. It can also be suitably used as a sealant.

Propylene Polymer

This invention provides a novel homopolymer of propylene or a copolymer of propylene with a copolymerizable comonomer (hereinafter referred to as "propylene polymer").

The propylene polymer of this invention fulfills the following properties (1) and (2).

Property (1): The isotactic triad ratio ($I_3$) should be in the range of 0.50–0.99.

Property (2): The proportion of the number of moles of the propylene unit originating from 2,1-insertion of the propylene monomer and that of the number of moles of the propylene unit originating from 1,3-insertion of the propylene monomer based on the total number of moles of the propylene unit forming the olefin polymer should be each less than 0.05 mol %.

The propylene polymer of this invention has the isotactic triad ratio ($I_3$) preferably in the range of 0.60–0.99, more preferably in the range of 0.80–0.94, and particularly preferably in the range of 0.85–0.93.

In the propylene polymer of this invention, the proportion of the number of moles of the propylene unit originating from 2,1-insertion of the propylene monomer and that of the number of moles of the propylene unit originating from 1,3-insertion of the propylene monomer are each preferably less than 0.04 mol %, particularly preferably less than 0.02 mol % based on the total number of moles of the propylene unit forming the olefin polymer.

The isotactic triad ratio ($I_3$) mentioned above, and the proportion of the number of moles of the propylene unit originating from 2,1-insertion of the propylene monomer and that of the number of moles of the propylene unit originating from 1,3-insertion of the propylene monomer based on the total number of moles of the propylene unit forming the olefin polymer are determined by the $^{13}$C-nuclear magnetic resonance spectrum determined in accordance with the method mentioned above.

The propylene polymer of this invention may have a melting point or may not. Owing to the properties mentioned above, the melting point of this propylene polymer is preferably in the range of 60–165° C., more preferably in the range of 70–155° C., and particularly preferably in the range of 130–150° C.

The melting point (Tm) is determined by using a DCS-7 differential scanning calorimeter manufactured by Perkin Elmer Inc. as described above.

The propylene polymer of this invention has the weight average molecular weight (Mw) in the range of 10,000–1,000,000 g/mol, preferably in the range of 80,000–500,000 g/mol, and more preferably in the range of 100,000–400,000 g/mol as determined by the gel permeation chromatography (GPC).

In the propylene polymer of this invention, the ratio of the weight average molecular weight (Mw) to the number average molecular weight (Mn), i.e., (Mw/Mn) is in the range of 1.5–3.8, preferably in the range of 1.5–3.5, more preferably in the range of 1.8–3.3, particularly preferably in the range of 1.8–3.0, and most preferably in the range of 1.8–2.5.

Further, the propylene polymer of this invention has a melt flow rate (based on JIS K7210 and determined under the condition 14 shown in Table 1) preferably in the range of 0.3–300 g/10 min, and more preferably in the range of 0.5–100 g/10 min.

Though the method for producing the propylene polymer of this invention is not particularly limited, the production is preferably carried out by using the metallocene catalyst shown in (1') below.

(1') Metallocene catalyst (homogeneous metallocene catalyst) comprising a metallocene compound (hereinafter referred to as "component (A1)" occasionally), an activating compound (component (B)), and optionally an organoaluminum compound (component (D)).

Preferred examples of the metallocene compound of the component (A') include dimethylsilylene bis(2-(2-thienyl)-4,5-dimethylcyclopentadienyl) zirconium dichloride and dimethylsilylene bis(2-(2-furyl)-4,5-dimethylcyclopentadienyl) zirconium dichloride, and further, the metallocene compounds represented by the formula (1).

Non-exclusive examples of the metallocene compound which can be advantageously used in the production of the propylene polymer of this invention include dimethylsilylene bis(2-(2-(5-methyl)-furyl)-indenyl) zirconium dichloride, dimethylsilylene bis(2-(2-(5-phenyl)-furyl)-indenyl) zirconium dichloride, dimethylsilylene bis(2-(2-(5-butyl)-furyl)-indenyl) zirconium dichloride, dimethylsilylene bis(2-(2-(5-trimethylsilyl)-furyl)-indenyl) zirconium dichloride, dimethylsilylene bis(2-(2-thienyl)-indenyl) zirconium dichloride, dimethylsilylene bis(2-(2-thienyl)-4,5-dimethylcyclopentadienyl) zirconium dichloride, dimethylsilylene bis(2-(2-furyl)-4,5-dimethyl-cyclopentadienyl) zirconium dichloride, dimethylsilylene bis(2-(2-(5-methyl)-thienyl)-indenyl) zirconium dichloride, dimethylsilylene bis(2-(2-(5-phenyl)-thienyl)-indenyl) zirconium dichloride, dimethylsilylene bis(2-(2-(5-t-butyl)-thienyl)-indenyl) zirconium dichloride, and dimethylsilylene bis(2-(2-(5-trimethylsilyl)-thienyl)-indenyl) zirconium dichloride.

Among the above metallocene compounds, particularly preferable are dimethylsilylene bis(2-(2-(5-methyl)-furyl)-indenyl) zirconium dichloride, dimethylsilylene bis(2-(2-(5-t-butyl)-furyl)-indenyl) zirconium dichloride, dimethylsilylene bis(2-(2-(5-trimethylsilyl)-furyl)-indenyl) zirconium dichloride, dimethylsilylene bis(2-(2-thienyl)-indenyl) zirconium dichloride, dimethylsilylene bis(2-(2-thienyl)-4,5-dimethylcyclopentadienyl) zirconium dichloride and dimethylsilylene bis(2-(2-furyl)-4,5-dimethyl-cyclopentadienyl) zirconium dichloride.

Among these metallocene compounds, the most preferably used are dimethylsilylene bis(2-(2-thienyl)-indenyl) zirconium dichloride, dimethylsilylene bis(2-(2-thienyl)-4,5-dimethylcyclopentadienyl) zirconium dichloride, dimethylsilylene bis(2-(2-furyl)-4,5-dimethyl-cyclopentadienyl) zirconium dichloride and dimethylsilylene bis(2-(2-(5-methyl)-furyl)-indenyl) zirconium dichloride.

As the component (B), an organoaluminum oxy compound or a compound which reacts with the component (A') to form an ion pair is used.

As the organoaluminum oxy compound, an aluminoxane represented by the formula (2) or (3) mentioned above is used.

The compound which reacts with the component (A') to form an ion pair include the same Lewis acids, ionic compounds, borane compounds and carbolan compounds as the compounds which react with the component (A) to form an ion pair as described for the olefin polymerization catalysts.

The component (D) optionally used in the uniform metallocene catalyst is the compounds represented by the formula: $AlR^4_sR^5_tX_{3-(s+t)}$, as described above.

For the production of the propylene polymer of this invention, any one of the known olefin polymerization processes (propylene polymerization processes) can be used, as described for the method for producing the olefin polymer.

The production of the propylene polymer of this invention is carried out at a polymerization temperature of −50 to 150° C., preferably 20 to 120° C., and more preferably 40 to 100° C. under a polymerization pressure in the range of atmospheric pressure to 9.9 MPa (gauge), preferably in the range of 0.4 to 5.0 MPa (gauge). Then, the produced propylene polymer may have the molecular weight adjusted by introducing such a chain transfer agent as hydrogen.

After the polymerization reaction, the propylene polymer is obtained by separating the unreacted monomer and hydrogen from the polymerization system and treating this system to inactivate the catalyst.

The propylene polymer of this invention may be incorporated therein with various additives such as antioxidant, ultraviolet absorber, antistatic agent, nucleating agent, lubricant, flame retardant, antiblocking agent, coloring agent, and inorganic or organic filler, and further, various synthetic resins, if necessary, then generally melted and kneaded with a melt-mixing device at a temperature of 190–350° C. for 20 seconds to 30 minutes, extruded into strands as required, and further pelletized. Thus, it is used in the form of pellets for the production of various molded articles.

Propylene/ethylene Copolymer

This invention further provides a novel propylene/ethylene copolymer.

Specifically, the propylene/ethylene copolymer of this invention is a propylene/ethylene copolymer produced by the use of an olefin polymerization catalyst and characterized by satisfying the following properties (1)–(3).

Property (1): The content of the ethylene unit should be in the range of 0.1–3.3% by weight.

Property (2): The isotactic triad ratio ($I_3$) should be not less than 0.50 and less than 0.95.

Property (3): The proportion of the number of moles of the propylene unit originating from 2,1-insertion of the propylene monomer should be not less than 0.05 and less than 0.5% based on the total number of moles of the propylene unit forming the propylene polymer.

The property (1) required for the propylene/ethylene copolymer of this invention is that the content of the ethylene unit should be in the range of 0.1–3.3% by weight, preferably in the range of 0.5–3.3% by weight, more preferably in the range of 1.0–3.3% by weight, and particularly preferably in the range of 2.0–3.0% by weight. If the content of the ethylene unit is less than 0.1% by weight, the copolymer will have an insufficient low-temperature heat-sealing property and transparency. If it is more than 3.3% by weight, the copolymer will have an insufficient stiffness and impact resistance.

The property (2) required for the propylene/ethylene copolymer of this invention is that the isotactic triad ratio ($I_3$) of this copolymer should be not less than 0.50 and less than 0.95, preferably not less than 0.70 and less than 0.95, and particularly preferably not less than 0.80 and less than 0.95.

The property (3) required for the propylene/ethylene copolymer of this invention is that the proportion of the number of moles of the propylene unit originating from 2,1-insertion of the propylene monomer should be not less than 0.05% and less than 0.5%, preferably not less than 0.05% and less than 0.45%, and more preferably not less than 0.1% and less than 0.4% based on the total number of moles of the propylene unit forming the propylene/ethylene copolymer. If the proportion of the number of moles of the propylene unit originating from 2,1-insertion of the propylene monomer is less than 0.05% based on the total number of moles of the propylene unit, the copolymer will have an insufficient low-temperature heat-sealing property and transparency. If this proportion exceeds 0.5%, the copolymer will have an insufficient stiffness and heat resistance.

Further, the proportion of the number of moles of the propylene unit originating from 1,3-insertion of the propylene monomer is preferably not more than 0.5%, preferably not more than 0.3%, particularly preferably not more than 0.2%, and most preferably not more than 0.05% based on the total number of moles of the propylene unit forming the propylene/ethylene copolymer of this invention.

The methods for determining the isotactic triad ratio ($I_3$) and the proportion of the number of moles of the propylene unit originating from 2,1-insertion of the propylene monomer and that of the number of moles of the propylene unit originating from 1,3-insertion of the propylene monomer based on the total number of moles of the propylene unit forming the propylene/ethylene copolymer are as described above.

Owing to the various properties mentioned above, the propylene/ethylene copolymer of this invention has a melting point preferably in the range of 100–150° C., more preferably in the range of 110–140° C., and particularly preferably in the range of 115–135° C.

The method for determining the melting point (Tm) is as described above.

The propylene/ethylene copolymer of this invention has the weight average molecular weight (Mw) preferably in the range of 10,000–1,000,000 g/mol, more preferably in the range of 80,000–500,000 g/mol, and most preferably in the range of 100,000–400,000 g/mol as determined by the gel permeation chromatography (GPC).

In the propylene/ethylene copolymer of this invention, the ratio of the weight average molecular weight (Mw) to the number average molecular weight, i.e., (Mw/Mn) is preferably in the range of 1.5–3.8, more preferably in the range of 1.5–3.5, and most preferably in the range of 1.8–2.5.

Further, the propylene/ethylene copolymer of this invention has a melt flow rate (based on JIS K7210 and determined under the condition 14 shown in Table 1) preferably in the range of 0.3–300 g/10 min, and more preferably in the range of 0.5–100 g/10 min. If the melt flow rate is lower than 0.3 g/10 min or higher than 300 g/10 min, the copolymer will have difficulty in molding by a known molding method.

The method of producing the propylene/ethylene copolymer of this invention is not particularly limited as far as the resultant copolymer has the above-described properties. Preferably, this copolymer can be produced by using either (1) the olefin polymerization catalyst formed of the supported metallocene catalyst I and an organoaluminum compound (component (D')) or (2) the olefin polymerization catalyst formed of the supported metallocene catalyst II and the component (D'). The preactivated supported metallocene catalysts I and II may also be used as described above.

In the production of the propylene/ethylene copolymer of this invention, the component (D') used in combination with the supported metallocene catalyst I or II is the same as described above.

The amount of the supported metallocene catalyst I or II or the preactivated supported metallocene catalyst I or II used for polymerization is in the range of $1 \times 10^{-10}$ to $1 \times 10^{-3}$ mol, preferably in the range of $1 \times 10^{-9}$ to $1 \times 10^{-4}$ mol in terms of the transition metal atom originating in the metallocene compound (A) contained in the catalyst per liter of the polymerization volume. The above-defined amount of the catalyst makes it possible to efficiently polymerize the olefin at a controlled velocity of polymerization reaction.

The process for producing the propylene/ethylene copolymer in this invention may be any one of the known processes. The method of slurry polymerization which polymerizes propylene in inert solvents, for example, aliphatic hydrocarbons such as butane, pentane, hexane, heptane and isooctane; alicyclic hydrocarbons such as cyclopentane, cyclohexane and methylcyclohexane; aromatic hydrocarbons such as toluene, xylene and ethylbenzene; gasoline fractions, and hydrogenated diesel oil fractions may be adopted. Further, the method of bulk polymerization which uses propylene itself as a solvent and the method of gas phase polymerization which implements the polymerization of propylene in a gas phase may be adopted. A combination of two or more of such polymerization processes can also be adopted. The most preferable combination is a combination of the first stage by the method of bulk polymerization with the subsequent second stage by the method of gas phase polymerization. Further, the method of solution polymerization can be used. Among these methods, the method of gas phase polymerization is used most favorably. Particularly, the method of gas phase polymerization which makes use of a horizontal reaction vessel provided with a stirrer rotatable on the horizontal axis is used most advantageously.

The production of the propylene/ethylene copolymer of this invention is carried out at a polymerization temperature of −50 to 150° C., preferably 20 to 120° C., and more preferably 40 to 100° C. under a polymerization pressure in the range of atmospheric pressure to 9.9 MPa (gauge), preferably in the range of 0.4 to 5.0 MPa (gauge). Then, the produced propylene/ethylene copolymer may have the molecular weight adjusted by introducing such a chain transfer agent as hydrogen.

After the polymerization reaction, the propylene polymer is obtained by separating the unreacted monomer and hydrogen from the polymerization system and treating this system to inactivate the catalyst.

The propylene/ethylene copolymer of this invention may be incorporated therein with various additives such as antioxidant, ultraviolet absorber, antistatic agent, nucleating agent, lubricant, flame retardant, antiblocking agent, coloring agent, and inorganic or organic filler, and further, various synthetic resins, if necessary, then generally melted and kneaded with a melt-mixing device at a temperature of 190–350° C. for 20 seconds to 30 minutes, extruded into strands as required, and further pelletized. Thus, it is supplied in the form of pellets for the production of various molded articles.

EXAMPLES

Now, this invention will be described more specifically below with reference to examples and comparative examples. It should be noted, however, that this invention is not limited thereto.

The definitions of the terms used in the examples and the comparative examples and the methods for determining the relevant magnitudes are shown below.

(1) The melt flow rate (MFR) (unit: g/10 min) was determined based on JIS K7210 under the condition 14 shown in Table 1 (under a load of 21.18N at 230° C.).
(2) The isotactic pentad ratio ($I_5$) was determined by the aforementioned method using "JEOL-GX270 (trade name)" manufactured by Japan Electron Optics Laboratory Co., Ltd.
(3) The isotactic triad ratio ($I_3$) was determined by the aforementioned method using "JEOL-GX270 (trade name)" manufactured by Japan Electron Optics Laboratory Co., Ltd.
(4) The proportion of the number of moles of the propylene unit originating from 2,1-insertion of the propylene monomer and that of the number of moles of the propylene unit originating from 1,3-insertion of the propylene monomer based on the total number of moles of the propylene unit forming the propylene/ethylene copolymer were determined by the aforementioned method using "JEOL-GX270 (trade name)" manufactured by Japan Electron Optics Laboratory Co., Ltd. The lower limit of the detection was 0.02 mol %.
(5) The weight average molecular weight (Mw) (unit: g/mol) of an olefin polymer was determined by the method of gel permeation chromatography (GPC) using a column "PSKgel GMH6-HT (trade name)" manufactured by Tosoh Corp. and a measuring instrument "GPC-150C (trade name)" manufactured by Waters Corp. In preparation for the determination, a test sample (olefin polymer) was dissolved in o-dichlorobenzene so that the concentration thereof should be 0.05% by weight and the resultant solution was heated to 135° C.
(6) The ratio of the weight average molecular weight (Mw) to the number average molecular weight (Mn), i.e., (Mw/Mn) was determined by the method of gel permeation chromatography (GPC) using a column "PSKgel GMH6-HT (trade name)" manufactured by Tosoh Corp. and a measuring instrument "GPC-150C (trade name)" manufactured by Waters Corp. In preparation for the determination, a test sample (olefin polymer) was dissolved in o-dichlorobenzene so that the concentration thereof should be 0.05% by weight and the resultant solution was heated to 135° C.
(7) The melting point (° C.) was determined by the method described above by using a DSC-7 differential scanning calorimeter manufactured by Perkin Elmer Inc.
(8) Intrinsic viscosity (η) (unit: dl/g) was determined in Tetralin as a solvent at a temperature of 135° C. by using an "AVS2 type" automatic viscometer manufactured by Mitsui-Toatsu Chemicals, Inc.
(9) The content (unit: % by weight) of the olefin unit in the propylene/olefin copolymer formed of propylene and an olefin other than propylene was determined by the $^{13}C$ NMR.

Example 1

[Synthesis of rac-dimethylsilylene bis(2-(2-(5-methyl)-furyl)-indenyl) zirconium dichloride]

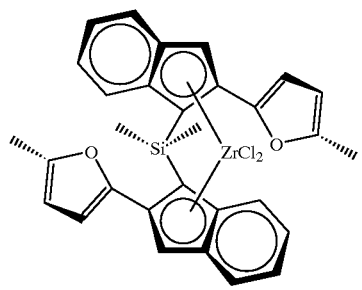

-continued

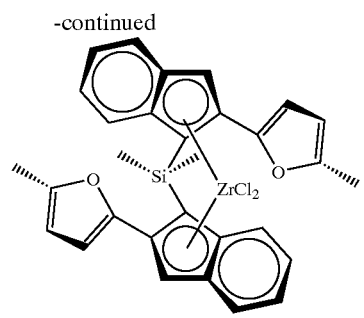

(1) Synthesis of 2-(2-(5-methyl-furyl)-indene

In a 500-ml glass reaction vessel, 20 g (0.24 mol) of 2-methyl-furan and 250 ml of THF were placed and cooled to −50° C. in a dry ice-methanol bath. To the cooled mixture, 160 ml (0.24 mol) of a 1.50 mol/L n-butyl lithium-hexane solution was added dropwise. After the dropwise addition, the mixture was allowed to warm to room temperature and stirred for 3 hours. The resultant mixture was again cooled to −30° C. in a dry ice-methanol bath and 100 ml of a THF solution containing 32 g (0.24 mol) of 2-indanone was added dropwise. After the dropwise addition, the mixture was allowed to warm to room temperature and stirred for 16 hours. The reaction solution was cooled to −20° C. in a dry ice-methanol bath and 100 ml of 2N hydrochloric acid was added dropwise. This solution was transferred to a separation funnel and washed with a saline solution until neutrality. Sodium sulfate anhydride was added, and the solution was allowed to stand overnight and dried. The sodium sulfate anhydride was filtered off, and the solvent was distilled off under reduced pressure. 600 ml of toluene and 0.5 g (2.6 mmol) of p-toluenesulfonic acid were added, and the solution was heated to reflux for one hour. The resultant reaction solution was transferred to a separation funnel and washed with a saline solution until neutrality. Sodium sulfate anhydride was added, and the solution was allowed to stand overnight and dried. The sodium sulfate anhydride was filtered off, and the solvent was distilled off under reduced pressure. The residue was purified by a silica gel column to obtain 22 g (yield 46%) of 2-(2-(5-methyl)-furyl)-indene as light yellow crystals. The structure was confirmed by NMR.

(2) Synthesis of Dimethyl bis(2-(2-(5-methyl)-furyl)-indenyl) Silane

In a 200-ml glass reaction vessel, 30 g (0.15 mol) of 2-(2-(5-methyl)-furyl)-indene, 0.9 g (7.4 mmol) of copper isocyanate and 300 ml of THF were placed and cooled to −70° C. in a dry ice-methanol bath. To the cooled mixture, 102 ml (0.15 mol) of a 1.50 mol/L n-butyl lithium-hexane solution was added dropwise. After the dropwise addition, the mixture was allowed to gradually warm to room temperature while stirring for 16 hours. The mixture was again cooled to −50° C. in a dry ice-methanol bath and 70 ml of a THF solution containing 9.9 g (0.077 mol) of dimethyl dichlorosilane was added thereto dropwise. After the dropwise addition, the mixture was allowed to gradually warm to room temperature while stirring for 16 hours. Distilled water was added to the reaction solution, which was transferred to a separation funnel and washed with a saline solution until neutrality. Sodium sulfate anhydride was added and the solution was allowed to stand overnight and dried. The sodium sulfate anhydride was filtered off, and the solvent was distilled off under reduced pressure. The residue was purified by a silica gel column and recrystallized from hexane to obtain 27 g (yield 78%) of dimethyl bis(2-(2-(5-methyl)-furyl)-indenyl) silane as colorless crystals.

(3) Synthesis of Dimethylsilylene bis(2-(2-(5-methyl)-furyl)-indenyl) Zirconium Dichloride In a 100-ml glass reaction vessel, 5.0 g (0.011 mol) of dimethyl bis(2-(2-(5-methyl)-furyl)-indenyl) silane and 100 ml of diethyl ether were placed and cooled to −70° C. in a dry ice-methanol bath. To the cooled mixture, 15 ml (0.023 mol) of a 1.50 mol/L n-butyl lithium-hexane solution was added dropwise. After the dropwise addition, the mixture was allowed to warm to room temperature and stirred for 16 hours. The reaction solution was concentrated under reduced pressure until the volume of the solvent decreased to about 20 ml. 170 ml of toluene was added and the solution was cooled to −70° C. in a dry ice-methanol bath. To the cooled solution, 2.6 g (0.012 mol) of zirconium tetrachloride was added. Thereafter, the solution was allowed to gradually warm room temperature while stirring for two days. The analysis of a part of the reaction solution by NMR failed to detect any discernible peak of a meso isomer. The solvent was distilled off under reduced pressure and the residue was recrystallized from toluene/hexane to obtain 2.8 g (yield 42%) of rac-dimethylsilylene bis(2-(2-(5-methyl)-furyl)-indenyl) zirconium dichloride as a metallocene compound (purity not less than 99%).

The $^1$H-NMR data (CDCl$_3$) of the metallocene compound were as shown below.

$^1$H-NMR (CDCl$_3$): δ 1.12 (s, 6H), δ 2.42 (s, 6H), δ 6.07 (d, 2H), δ 6.27 (d, 2H), δ 6.71 (t, 2H), δ 6.92 (s, 2H), δ 6.92 (d, 2H), δ 7.31 (t, 2H), δ 7.54 (d, 2H).

[Production of Propylene Homopolymer by the use of Rac-dimethylsilylene bis(2-(2-(5-methyl)-furyl)-indenyl) Zirconium Dichloride]

In a SUS autoclave, 1 liter of toluene, a methyl aluminoxane-toluene solution "MMAO3A (trade name)" (Al/Zr=10,000) made by Tosoh-Akzo Corp. and 3 ml (0.34× $10^{-6}$ mol) of a dimethylsilylene bis(2-(2-(5-methyl)-furyl)-indenyl) zirconium dichloride-toluene solution were sequentially added and heated to 30° C. To the resultant mixture, propylene was introduced under a pressure of 0.3 MPa, and polymerization was carried out for one hour. After the polymerization, the polymer was filtered and washed with 1 liter of hydrochloric methanol to decompose the catalyst component. It was filtered, washed, and dried sequentially to obtain 8.7 g of propylene homopolymer. The polymerization activity was 26 kg-polymer/mmol(Zr)·hr. As the result of the analysis of the propylene homopolymer, the MFR was 0.004 g/10 min, the isotactic pentad ratio ($I_5$) was 0.928, the isotactic triad ratio ($I_3$) was 0.946, and the proportion of the number of moles of the propylene unit originating from 2,1-insertion of the propylene monomer and that of the number of moles of the propylene unit originating from 1,3-insertion of the propylene monomer each was less than 0.02 mol %, i.e., less than the lower limit of detection based on the total number of moles of the propylene unit forming the propylene homopolymer, the Mw was 1.61×10$^6$ g/mol, the Mw/Mn was 3.0, and the melting point was 146.2° C.

COMPARATIVE EXAMPLE 1

Synthesis of Rac-dimethylsilylene bis(2-methyl-indenyl) Zirconium Dichloride

The rac-dimethylsilylene bis(2-methyl-indenyl) zirconium dichloride was synthesized by the method disclosed in U.S. Pat. No. 5,145,819 (EP0485823, JP-A-4-300887).

[Production of Propylene Homopolymer by the use of Rac-dimethylsilylene bis(2-methyl-indenyl) Zirconium Dichloride as a Catalyst]

In a SUS autoclave, one liter of toluene, a methyl aluminoxane-toluene solution "MMAO3A (trade name)"

(Al/Zr=10,000) made by Tosoh-Akzo Corp. and 3 ml (0.42× $10^{-6}$ mol) of rac-dimethylsilylene bis(2-methyl-indenyl) zirconium dichloride-toluene solution were sequentially added and heated to 30° C. To the resultant mixture, propylene was introduced under a pressure of 0.3 MPa and polymerization was carried out for one hour. After the polymerization, the polymer was filtered and washed with 1 liter of hydrochloric methanol to decompose the catalyst component. Thereafter, the polymer was filtered, washed, and dried sequentially to obtain 19.5 g of propylene homopolymer. The polymerization activity was 46 kg-polymer/mmol(Zr)·hr.

As the result of the analysis of the propylene homopolymer, the MFR was 0.53 g/10 min, the isotactic pentad ratio ($I_5$) was 0.945, the isotactic triad ratio ($I_3$) was 0.961, the proportion of the number of moles of the propylene unit originating from 2,1-insertion of the propylene monomer was 0.29 mol % and the proportion of the number of moles of the propylene unit originating from 1,3-insertion of the propylene monomer was less than 0.02 mol %, each less than the lower limit of detection based on the total number of moles of the propylene unit forming the propylene homopolymer, the Mw was $3.48 \times 10^5$ g/mol, the Mw/Mn was 1.9, and the melting point was 153.1° C.

Example 2

Production of Propylene/ethylene Copolymer by the use of Rac-dimethylsilylene bis(2-(2-(5-methyl)-furyl)-indenyl) Zirconium Dichloride In a 1.5-liter autoclave thoroughly purged with nitrogen, 900 ml of hexane and 1 mmol of triisobutyl aluminum were placed. The mixture was heated to 70° C. while stirring, then fed with ethylene and pressurized to 0.19 MPa, fed with propylene and brought to a total pressure of 0.58 MPa. Thereafter, a metallocene catalyst, which was obtained in advance by mixing 0.001 mmol per Zr atom of the rac-dimethylsilylene bis(2-(2-(5-methyl)-furyl0-indenyl) zirconium dichloride synthesized in Example 1 as a metallocene compound and 0.3 mmol in terms of Al atom of methylaluminoxane "p-MAO" made by Tosoh-Akzo Corp. for 10 minutes, was introduced under the pressure of propylene. Polymerization was carried out for 10 minutes at 70° C. under a fixed pressure, with propylene continuously fed to maintain the total pressure at 0.78 MPa. After 10 minutes, the unreacted monomer was removed by degassing and the produced polymer was collected in a large volume of methanol. The polymer was dried with a vacuum drier to have a fixed weight. Thus, 3.4 g of the polymer was obtained.

The polymerization activity was 20.2 kg-polymer/(mmol-Zr·h). As the result of the analysis of the propylene/ethylene copolymer, the content of the ethylene unit was 20.9% by weight (28.4 mol %), the isotactic triad ratio ($I_3$) was 0.899, the proportion of the number of moles of the propylene unit originating from 2,1-insertion and the proportion of the number of moles of the propylene unit originating from 1,3-insertion each was less than 0.02 mol %, i.e., less than the limit of detection, the intrinsic viscosity [η] was 1.52 dl/g, the weight average molecular weight (Mw) was 156000, and the ratio of the weight average molecular weight (Mw) to the number average molecular weight (Mn), i.e., (Mw/Mn) was 2.24.

Example 3

Production of Preactivated Supported Metallocene Catalyst by the use of Rac-dimethylsilylene bis(2-(2-(5-methyl)-furyl)-indenyl) Zirconium Dichloride and Production of Propylene Homopolymer

[Production of Preactivated Supported Metallocene Catalyst]

(1) Production of Supported Metallocene Catalyst

In a 500-ml glass reaction vessel purged with nitrogen gas and equipped with a stirrer, 89 ml (267 mmol in terms of Al atom) of a toluene solution of methyl aluminoxane (concentration: 3 mol/liter, "PMAO (trade name)" made by Tosoh-Akzo Corp.) and 0.929 mmol of chiral dimethylsilylene bis(2-(2-(5-methyl)-furyl)-indenyl) zirconium dichloride as an ansa-metallocene compound were placed and reacted while stirring at 25° C. for 15 minutes to obtain the reaction product of the metallocene compound and the aluminoxane, i.e., a metallocene catalyst.

Subsequently, the reaction vessel was charged with 6.7 g of silica having an average particle diameter of 51 μm ("SYLOPOL® 948" made by Grace Davison), which had been calcined in advance under reduced pressure at 750° C. for eight hours. The temperature of the reaction vessel was elevated to 110° C., and kept for 60 minutes while stirring the reaction product and the silica to carry out a catalytic reaction, which gives a slurry containing a supported metallocene catalyst having the aforementioned metallocene catalyst deposited thereon.

The reaction vessel was cooled to −10° C., fed with 250 ml of n-hexane and stirred for 10 minutes while kept at −10° C. Thereafter, the stirrer was stopped and the solvent was separated by decantation. Subsequently, the reaction vessel was kept at −10° C., fed with 250 ml of n-hexane and washed by stirring for five minutes. Thereafter, the stirrer was stopped and the washing operation by decantation for the separation of the cleaning solvent was performed four times to obtain a purified supported metallocene catalyst. The reaction vessel was further fed with 250 ml of n-hexane to disperse the supported metallocene catalyst, which gives a slurry.

(2) Production of Preactivated Supported Metallocene Catalyst

The slurry of the supported metallocene catalyst and n-hexane obtained in (1) above was transferred into a 500-ml glass reaction vessel purged with nitrogen gas and equipped with a stirrer, and the temperature of the reaction vessel was adjusted to 0° C. While stirring at 0° C., a propylene/hydrogen mixed gas having a molar ratio of 10:1 was supplied to the reaction vessel at a feed rate of 300 ml/minute for 40 minutes and prepolymerization was carried out. The formed propylene homopolymer was supported on the aforementioned supported metallocene catalyst.

The used n-hexane solvent was separated from the reaction mixture by decantation, then 250 ml of n-hexane was added, and the mixture was stirred for five minutes to wash the preactivated supported metallocene catalyst. The washing operation for the separation of the cleaning solvent by decantation was performed five times. Then, the reaction vessel was fed with 250 ml of n-hexane to disperse the produced preactivated supported metallocene catalyst, which gives a slurry. The slurry of the preactivated supported metallocene catalyst and n-hexane was filtered to separate the solvent and then dried under reduced pressure at 25° C. to obtain a preactivated supported metallocene catalyst as solid particles. The preactivated supported metallocene catalyst thus obtained was analyzed. 1 g of the propylene polymer was deposited per g of the supported catalyst prior to the preactivation.

[Production of Propylene Homopolymer]

A 3-liter horizontal gas phase reaction vessel thoroughly purged with nitrogen was heated to 70° C. and charged with 150 g of crude powder of polypropylene and 0.5 mmol of triethyl aluminum, which were stirred at 85 rpm for five minutes. Then, the preactivated supported metallocene catalyst prepared as described above was added in an amount of 87 mg in terms of the supported catalyst prior to the preactivation, which was stirred for another five minutes. Subsequently, the reaction vessel was fed with propylene monomer, the reaction pressure was increased to 2.3 MPa (gauge), and the monomer was polymerized under fixed conditions, i.e., at 70° C. and 2.3 MPa (gauge). The supply of the monomer was stopped when the amount of the formed propylene homopolymer reached 300 g. The reaction vessel was decompressed to atmospheric pressure. 300 g of a powdery polymer was extracted from the reaction vessel under nitrogen flow.

Subsequently, the same polymerization was carried out twice as the procedure described above except that 150 g of the powdery polymer remaining in the reaction vessel after the extraction was used in the place of 150 g of the crude powder of polypropylene. Based on the results of the third polymerization, the polymerization activity was calculated and the produced propylene homopolymer was analyzed. The polymerization time was about 1.5 hours in each round.

From the results described above, the polymerization activity was 1720 g·polymer/g·catalyst per g of the supported catalyst prior to the preactivation. As the result of the analysis of the propylene homopolymer, the weight average molecular weight (Mw) was 2.05×10$^5$ g/mol, the ratio of the weight average molecular weight (Mw) to the number average molecular weight (Mn), i.e., (Mw/Mn) was 2.4, the MFR was 6 g/10 minutes, the melting point was 137° C., the isotactic pentad ratio ($I_5$) was 0.869, the isotactic triad ratio ($I_3$) was 0.906, the proportion of the number of moles of the propylene unit originating from 2,1-insertion of the propylene monomer was 0.36 mol % based on the total number of moles of the propylene unit forming the propylene homopolymer, and the proportion of the number of moles of the propylene unit originating from 1,3-insertion of the propylene monomer was 0.18 mol % based on the total number of moles of the propylene unit forming the propylene homopolymer.

Example 4

Production of Propylene/ethylene Copolymer by use of a Preactivated Supported Metallocene Catalyst using Rac-dimethylsilylene bis(2-(2-(5-methyl)-furyl)-indenyl) Zirconium Dichloride A propylene/ethylene copolymer was produced in the same manner as in Example 3 except that a propylene/ethylene mixed monomer was supplied into the reaction vessel as the monomer so as to adjust the ethylene monomer concentration in the reaction vessel was 2.8 mol %.

The polymerization activity was 2300 g·polymer/g·catalyst per g of the supported catalyst prior to the preactivation. As the result of the analysis of the propylene/ethylene copolymer, the weight average molecular weight (Mw) was 2.01×10$^5$ g/mol, the ratio of the weight average molecular weight (Mw) to the number average molecular weight (Mn), i.e., (Mw/Mn) was 2.5, the MFR was 6.6 g/10 minutes, the content of the ethylene unit was 2.0% by weight, the melting point was 122° C., the isotactic triad ratio ($I_3$) was 0.913, and the proportion of the number of moles of the propylene unit originating from 2,1-insertion of the propylene monomer was 0.41 mol % based on the total number of moles of the propylene unit forming the propylene/ethylene copolymer, and the proportion of the number of moles of the propylene unit originating from 1,3-insertion of the propylene monomer was less than 0.02 mol %, i.e., less than the limit of detection based on the total number of moles of the propylene unit forming the propylene/ethylene copolymer.

Example 5

Synthesis of Rac-dimethylsilylene bis(2-(2-(5-methyl)-furyl)-4-phenyl-indenyl) Zirconium Dichloride

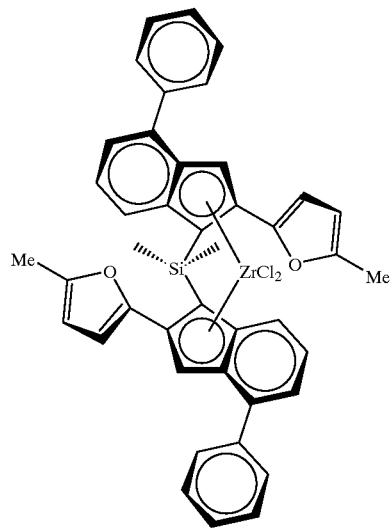

(1) Synthesis of dimethylsilylene bis(2-(2-(5-methyl)-furyl)-4-phenyl-indenyl) Silane In a 200-ml glass reaction vessel, 12 g (0.045 mol) of 2-(2-(5-methyl)-furyl)-4-phenyl-indene, 0.3 g (2.5 mmol) of copper isocyanate and 150 ml of THF were placed and cooled to −70° C. in a dry ice-methanol bath. To the cooled mixture, 30 ml (0.045 mol) of a 1.50 mol/L n-butyl lithium-hexane solution was added dropwise. After the dropwise addition, the mixture was allowed to gradually warm to room temperature while stirring for 16 hours. It was again cooled to −50° C. in a dry ice-methanol bath and 40 ml of a THF solution containing 2.9 g (0.022 mol) of dimethyl dichlorosilane was added dropwise thereto. After the dropwise addition, the mixture was allowed to gradually warm to room temperature while stirring for 16 hours.

Distilled water was added to the reaction solution, which was transferred to a separation funnel and washed with a saline solution until neutrality. Sodium sulfate anhydride was added to the solution, which was allowed to stand overnight and dried. The sodium sulfate anhydride was filtered off and the solvent was distilled off under reduced pressure. The residue was purified with a silica gel column to obtain 11 g (yield 82%) of dimethyl bis(2-(2-(5-methyl)-furyl)-4-phenyl-indenyl) silane as a pale yellow liquid.

(2) Synthesis of Rac-dimethylsilylene bis(2-(2-(5-methyl)-furyl)-4-phenyl-indenyl) Zirconium Dichloride In a 100-ml glass reaction vessel, 5.3 g (8.8 mmol) of dimethyl bis(2-(2-(5-methyl)-furyl)-4-phenyl-indenyl) silane and 150 ml of diethyl ether were placed and cooled to −70° C. in a dry ice-methanol bath. To the cooled mixture, 12 ml (18 mmol) of a 1.50 mol/L n-butyl lithium-hexane solution was added dropwise. After the dropwise addition, the mixture was allowed to warm to room temperature and stirred for 16 hours. The reaction solution was concentrated under reduced pressure until the amount of the solvent reached about 20 ml. 200 ml of toluene was added, and the solution was cooled to −70° C. in a dry ice-methanol bath. To the cooled mixture, 2.0 g (8.6 mmol) of zirconium tetrachloride was added. Thereafter, the mixture was allowed to gradually warm to room temperature while stirring for three days. The analysis of a part of the reaction solution by NMR failed to detect any discernible peak of a meso isomer.

The solvent was distilled off under reduced pressure and the residue was recrystallized from dichloromethane/hexane to obtain 3.0 g (yield 45%) of the racemic form (purity not less than 99%) of dimethylsilylene bis(2-(2-(5-methyl)-furyl)-4-phenyl-indenyl) zirconium dichloride as yellowish orange crystals.

$^1$H-NMR (CDCl$_3$) Racemic form: δ 1.15 (s, 6H), δ 2.42 (s, 6H), δ 6.06 (d, 2H), δ 6.26 (d, 2H), δ 6.81 (dd, 2H), δ 6.93 (d, 2H), δ 7.03 (s, 2H), δ 7.31–6 7.64 (m, 12H).

[Production of Propylene Homopolymer by the use of Rac-dimethylsilylene bis(2-(2-(5-methyl)-furyl)-4-phenyl-indenyl) Zirconium Dichloride as a Catalyst]

In an SUS autoclave, 1 liter of toluene, a methyl aluminoxane-toluene solution ("MMAO3A" made by Tosoh-Akzo Corp.) (Al/Zr=10,000) and 3 ml (0.29×10$^{-6}$ mol) of a rac-dimethylsilylene bis(2-(2-(5-methyl)-fury)-4-phenyl-indenyl) zirconium dichloride-toluene solution were sequentially placed and heated to 30° C. To the resultant mixture, propylene was introduced under a pressure of 0.3 MPa and polymerization was carried out for one hour. After the polymerization, the polymer was separated by filtration and the catalyst component was decomposed with 1 liter of hydrochloric methanol. Thereafter, the polymer was filtered, washed, and dried sequentially to obtain 32 g of a propylene homopolymer. The polymerization activity was 110 kg-polymer/mmol(Zr)·hr. As the result of the analysis of the propylene homopolymer, the MFR was 0.03 g/10 minutes, the isotactic pentad ratio ($I_5$) was 0.973, the isotactic triad ratio ($I_3$) was 0.985, the proportion of the number of moles of the propylene unit originating from 2,1-insertion of the propylene monomer was 0.22 mol % based on the total number of moles of the propylene unit forming the propylene homopolymer and the proportion of the number of moles of the propylene unit originating from 1,3-insertion of the propylene monomer was 0.05 mol % based on the total number of moles of the propylene unit forming the propylene homopolymer, the Mw was 7.33×10$^5$ g/mol, the Mw/Mn was 2.22, and the melting point was 159.1° C.

Example 6

Synthesis of Dimethylsilylene bis(2-(2-(5-methyl)-furyl)-4,5-benzoindenyl) Zirconium Dichloride

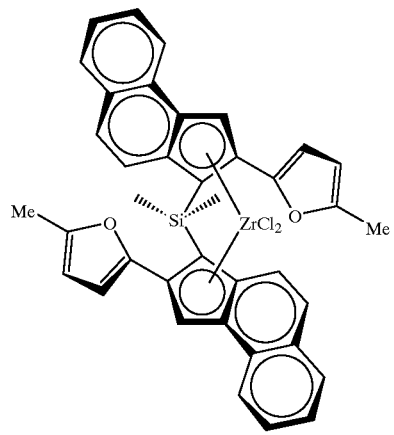

(1) Synthesis of Dimethyl bis(2-(2-(5-methyl)-furyl)-4,5-benzoindenyl) Silane

In a 200-ml glass reaction vessel, 23 g (0.095 mol) of 2-(2-(5-methyl)-furyl)-4,5-benzoindene, 0.4 ml (5.0 mmol) of 1-methylimidazole and 150 ml of THF were placed and cooled to −70° C. in a dry ice-methanol bath. To the cooled mixture, 60 ml (0.095 mol) of a 1.59 mol/L n-butyl lithium-hexane solution was added dropwise. After the dropwise addition, the mixture was allowed to gradually warm to room temperature while stirring for 16 hours. The mixture was again cooled to −50° C. in a dry ice-methanol bath and 50 ml of a THF solution containing 6.1 g (0.047 mol) of dimethyldichloro-silane was added dropwise. After the dropwise addition, the mixture was allowed to gradually warm to room temperature while stirring for 16 hours.

Distilled water was added to the reaction solution, which was transferred to a separation funnel and washed with a saline solution until neutrality. Sodium sulfate anhydride was added to the resultant solution, which was allowed to stand overnight and dried. The sodium sulfate anhydride was filtered off and the solvent was distilled off under reduced pressure. The residue was purified with a silica gel column to obtain 15.2 g (yield 59%) of dimethyl bis(2-(2-(5-methyl)-furyl)-4,5-benzoindenyl) silane as a pale yellow solid.

(2) Synthesis of Dimethylsilylene bis(2-(2-(5-methyl)-furyl)-4,5-benzoindenyl) Zirconium Dichloride In a 100-ml glass reaction vessel, 5.1 g (9.3 mmol) of dimethyl bis(2-(2-(5-methyl)-furyl)-4,5-benzoindenyl) silane and 180 ml of diethyl ether were placed and cooled to −70° C. in a dry ice-methanol bath. To the cooled mixture, 12 ml (19 mmol) of a 1.59 mol/L n-butyl lithium-hexane solution was added dropwise. After the dropwise addition, the mixture was allowed to warm to room temperature and stirred for 16 hours. The reaction solution was concentrated under reduced pressure until the amount of the solvent reached about 20 ml. 200 ml of toluene was added and the solution was cooled to −70° C. in a dry ice-methanol bath. To the cooled mixture, 2.2 g (9.3 mmol) of zirconium tetrachloride was added. Thereafter, the mixture was allowed to gradually warm to room temperature while stirring for 16 hours.

The solvent was distilled off under reduced pressure and the residue was recrystallized from dichloromethane/hexane to obtain 0.5 g (yield 7.8%) of the racemic form (purity not less than 99%) of dimethylsilylene bis(2-(2-(5-methyl)-furyl)-4,5-benzoindenyl) zirconium dichloride as yellow crystals.

$^1$H-NMR (CDCl$_3$) Racemic form: δ 1.14 (s, 6H), δ 2.46 (s, 6H), δ 6.13 (d, 2H), δ 6.34 (d, 2H), δ 6.87 (d, 2H), δ 6.96 (d, 2H), δ 7.40 (s, 2H), δ 7.48–6 7.55 (m, 4H), δ 7.72 (d, 2H), δ 7.99 (d, 2H).

[Propylene Polymerization by use of Dimethylsilylene bis(2-(2-(5-methyl)-furyl)-4,5-benzoindenyl) Zirconium Dichloride]

In a SUS autoclave, 1 liter of toluene, a methylaluminoxane-toluene solution ("MMAO3A" made by Tosoh-Akzo Corp.) (Al/Zr=10,000) and 3 ml (0.28×10$^{-6}$ mol) of dimethylsilylene bis(2-(2-(5-methyl)-furyl)-4,5-benzoindenyl) zirconium dichloride-toluene solution were placed sequentially and heated to 30° C. To the mixture, propylene was introduced under a pressure of 0.3 MPa and polymerization was carried out for one hour. After the polymerization, the polymer was separated by filtration and washed with 1 liter of hydrochloric methanol to decompose the catalyst component. Thereafter, the polymer was filtered, washed, and dried sequentially to obtain 6.9 g of polypropylene. The polymerization activity was 25 kg-polymer/mmol(Zr)·hr. As the result of the analysis of the propylene homopolymer, the MFR was 0.04 g/10 minutes, the isotactic pentad ratio ($I_5$) was 0.930, the isotactic triad ratio ($I_3$) was 0.9514, the proportion of the number of moles of the propylene unit originating from 2,1-insertion of the propylene monomer was 0.43 mol % based on the total number of moles of the propylene unit forming the propylene homopolymer and the proportion of the number of moles of the propylene unit originating from 1,3-insertion of the propylene monomer was less than 0.02 mol %, i.e., less than the limit of detection based on the total number of moles of the propylene unit forming the propylene homopolymer, the Mw was 8.97×10$^5$ g/mol, the Mw/Mn was 2.88, and the melting point was 150.2° C.

Example 7

Synthesis of the Dimethylsilylene bis(2-(2-(5-phenyl)-furyl)-indenyl) Zirconium Dichloride

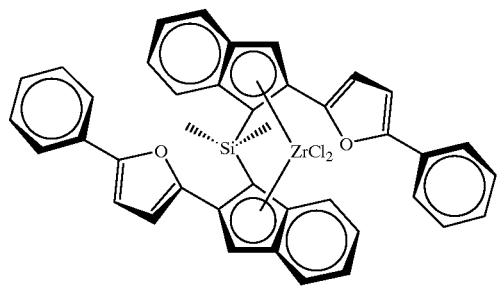

(1) Synthesis of 2-(2-(5-phenyl)-furyl)-indene

In a 1000-ml glass reaction vessel, 33 g (0.23 mol) of 2-phenylfuran and 300 ml of THF were placed and cooled to −70° C. in a dry ice-methanol bath. To the cooled mixture, 147 ml (0.23 mol) of a 1.56 mol/L n-butyllithium-hexane solution was added dropwise. After the dropwise addition, the mixture was allowed to warm to room temperature while stirring for 4 hours. The mixture was again cooled to −70° C. in a dry ice-methanol bath and 100 ml of a THF solution containing 30 g (0.23 mol) of 2-indanone was added dropwise. After the dropwise addition, the mixture was allowed to gradually warm to room temperature while stirring for 16 hours.

The reaction solution was cooled to −20° C. in the dry ice-methanol bath, and 100 ml of 4N-hydrochloric acid was added dropwise. The reaction solution was transferred to a separation funnel and washed with a saline solution until neutrality. Sodium sulfate anhydride was added to the reaction solution, which was allowed to stand overnight and dried. The sodium sulfate anhydride was filtered off and the solvent was distilled off under reduced pressure. 600 ml of toluene and 0.5 g (2.6 mmol) of p-toluene sulfonic acid were added, and the solution was heated to reflux for 1 hour. The reaction solution was transferred to a separation funnel and washed with a saline solution until neutrality. Sodium sulfate anhydride was added to the solution, which was allowed to stand overnight and dried. The sodium sulfate anhydride was filtered off and the solvent was distilled off under reduced pressure. The residue was purified with a silica gel column to obtain 19 g (yield 31%) of 2-(2-(5-phenyl)-furyl)-indene as colorless needle crystals. The structure was confirmed by NMR.

(2) Synthesis of Dimethyl bis(2-(2-(5-phenyl)-furyl)-indenyl) Silane

In a 200-ml glass reaction vessel, 19 g (72 mmol) of 2-(2-(5-phenyl)-furyl)-indene and 300 ml of THF were placed and cooled to −70° C. in a dry ice-methanol bath. To the cooled mixture, 102 ml (0.15 mol) of a 1.56 mol/L n-butyl lithium-hexane solution was added dropwise. After the dropwise addition, the mixture was allowed to gradually warm to room temperature while stirring for 16 hours. The reaction solution was again cooled to −70° C. in the dry ice-methanol bath. To the cooled mixture, 0.3 ml (3.6 mmol) of 1-methyl imidazole was added, and 70 ml of a THF solution containing 4.6 g (36 mmol) of dimethyl dichlorosilane was added dropwise. Thereafter, the mixture was allowed to gradually warm to room temperature while stirring for 16 hours.

Distilled water was added to the resultant solution, which was transferred to a separation funnel and washed with a saline solution until neutrality. Sodium sulfate anhydride was added to the resultant solution, which was allowed to stand overnight and dried. The sodium sulfate anhydride was filtered off and the solvent was distilled off under reduced pressure. The residue was recrystallized from dichloromethane/hexane to obtain 17 g (yield 82%) of dimethyl bis(2-(2-(5-phenyl)-furyl)-indenyl) silane as light yellow crystals.

(3) Synthesis of Dimethylsilylene bis(2-(2-(5-phenyl)-furyl)-indenyl) Dichloride In a 500-ml glass reaction vessel, 9.0 g (17 mmol) of dimethyl bis(2-(2-(5-phenyl)-furyl)-indenyl) silane, 100 ml of toluene and 150 ml of diethyl ether were placed and cooled to −70° C. in the dry ice-methanol bath. To the cooled mixture, 20 ml (32 mmol) of a 1.56 mol/L n-butyl lithium-hexane solution was added dropwise. After the dropwise addition, the mixture was allowed to warm to the room temperature and stirred for 16 hours. The reaction solution was concentrated under reduced pressure until the amount of the solvent reached about 20 ml. 300 ml of toluene was added and the solution was cooled to −70° C. in the dry ice-methanol bath. 3.7 g (16 mmol) of zirconium tetrachloride was added thereto. Thereafter, the mixture was allowed to gradually warm to room temperature while stirring overnight. As a result of measurement of $^1$H-NMR, the racemic/meso ratio in resulting crude complex was 81/19.

The solvent was distilled off under reduced pressure and the residue was recrystallized from the dichloromethane/hexane to obtain 2.2 g (yield 19%) of the racemic form (purity not less than 99%) of dimethylsilylene bis(2-(2-(5-phenyl)-furyl)-indenyl) zirconium dichloride.

$^1$H-NMR (CDCl$_3$) Racemic form: δ 1.12 (s, 6H), δ 6.53 (d, 2H), δ 6.73 (t, 2H), δ 6.77 (d, 2H), δ 6.97 (d, 2H), δ 7.03 (s, 2H), δ 7.32 (t, 2H), δ 7.35 (t, 2H), δ 7.45 (t, 4H), δ 7.59 (d, 2H), δ 7.74 (d, 4H).

[Production of Propylene Homopolymer by use of Dimethylsilylene bis(2-(2-(5-phenyl)-furyl)-indenyl) Zirconium Dichloride as a Catalyst]

In a SUS autoclave, 1 liter of toluene, a methylaluminoxane-toluene solution ("MMAO3A" made by Tosoh-Akzo Corp.) (Al/Zr=10,000) and 3 ml (0.30×10$^{-6}$ mol) of dimethylsilylene bis(2-(2-(5-phenyl)-furyl)-indenyl) zirconium dichloride-toluene solution were placed sequentially and heated to 30° C. To the mixture, propylene was introduced under a pressure of 0.3 MPa and polymerization was carried out for one hour. After the polymerization, the polymer was separated by filtration and washed with 1 liter of hydrochloric methanol to decompose the catalyst component. Thereafter, the polymer was filtered, washed, and dried sequentially to obtain 2.7 g of polypropylene. The polymerization activity was 9 kg-polymer/mmol(Zr)·hr. As the result of the analysis of the propylene homopolymer, the MFR was 0.01 g/10 minutes, the isotactic pentad ratio (I$_5$) was 0.9354, the isotactic triad fraction (I$_3$) was 0.9541, the proportion of the number of moles of the propylene unit originating from 2,1-insertion of the propylene monomer was less than the detection limit value, i.e., less than 0.02 mol % based on the total number of moles of the propylene unit forming the propylene homopolymer and the proportion of the number of moles of the propylene unit originating from 1,3-insertion of the propylene monomer was less than the detection limit value, i.e., less than 0.02 mol % based on the total number of moles of the propylene unit forming the propylene homopolymer, the Mw was 1.06×10$^6$ g/mol, the Mw/Mn was 2.47, and the melting point was 149.7° C.

Example 8

Production of Propylene/ethylene Copolymer by use of a Preactivated Supported Metallocene Catalyst using Rac-dimethylsilylene bis(2-(2-(5-methyl)-furyl)-4-phenyl-indenyl) Zirconium Dichloride In a 1.5-liter reaction vessel thoroughly purged with nitrogen, 0.5 mmol of triethylaluminium, 1.35 mmol of hydrogen and 800 ml of liquefied propylene were charged and heated to 50° C. in order to stabilize the resultant mixture. At this stage, the pressure in the vessel was 2.03 MPa (gauge). Then, ethylene was fed into the vessel until the pressure reached 2.13 MPa (gauge), i.e., 0.1 MPa higher than the pressure before this ethylene feed, so that the temperature and pressure conditions are further stabilized in the reaction vessel. Then, 84 mg of the preactivated supported metallocene catalyst prepared in accordance with the method described in Example 3 was fed to the reaction vessel, accompanied by 200 ml of propylene chloride, in order to initiate polymerization reaction. Thereafter, the copolymerization reaction of propylene and ethylene was carried out over 30 minutes at 50° C.

As a result, 135 g of propylene/ethylene copolymer was obtained. The polymerization activity was 6430 g·polymer/g·catalyst per g of the supported catalyst prior to the preactivation. As the result of the analysis of the produced propylene/ethylene copolymer, the MFR was 1.4 g/10 minutes, the content of ethylene units was 3.5% by weight, and the melting point was 124° C.

What is claimed is:

1. A metallocene compound selected from the group consisting of dimethylsilylene bis(2-(2-(5-methyl)-furyl)-indenyl) zirconium dichloride, dimethylsilylene bis(2-(2-(5-t-butyl)-furyl)-indenyl) zirconium dichloride, dimethylsilylene bis(2-(2-(5-trimethylsilyl)-furyl)-indenyl zirconium dichloride, dimethylsilylene bis(2-(2-(5-phenyl)-furyl)-indenyl) zirconium dichloride, dimethylsilylene bis(2-(2-(5-methyl)-thienyl)-indenyl) zirconium dichloride, dimethylsilylene bis-(2-(2-(5-t-butyl)-thienyl)-indenyl) zirconium dichloride, dimethylsilylene bis(2-(2-(5-trimethylsilyl)-thienyl)-indenyl) zirconium dichloride, dimethylsilylene bis(2-(2-(5-phenyl)-thienyl)-indenyl) zirconium dichloride, dimethylsilylene bis(2-(2-(5-methyl)-furyl)-4-phenyl)-indenyl) zirconium dichloride, dimethylsilylene bis(2-(2-(5-t-butyl)-furyl)-4-phenyl)-indenyl) zirconium dichloride, dimethylsilylene bis(2-(2-(5-trimethylsilyl)-furyl)-4-phenyl)-indenyl) zirconium dichloride, dimethylsilylene bis(2-(2-(5-phenyl)-furyl)-4-phenyl)-indenyl) zirconium dichloride, dimethylsilylene bis(2-(2-(5-methyl)-thienyl)-4-phenyl)-indenyl), zirconium dichloride, dimethylsilylene bis(2-(2-(5-t-butyl)-thienyl)-4-phenyl)-indenyl) zirconium dichloride, dimethylsilylene bis(2-(2-(5-trimethylsilyl)-thienyl)-4-phenyl)-indenyl) zirconium dichloride, dimethylsilylene bis(2-(2-(5-phenyl)-thienyl)-4-phenyl)-indenyl) zirconium dichloride, dimethylsilylene bis(2-(2-(5-methyl)-furyl)-4,5-benzoindenyl) zirconium dichloride, dimethylsilylene bis(2-(2-(5-t-butyl)-furyl)-4,5-benzoindenyl) zirconium dichloride, dimethylsilylene bis(2-(2-(5-trimethylsilyl)-furyl)-4,5-benzoindenyl) zirconium dichloride, dimethylsilylene bis(2-(2-(5-phenyl)-furyl)-4,5-benzoindenyl) zirconium dichloride, dimethylsilylene bis(2-(2-(5-methyl)-thienyl)-4,5-benzoindenyl) zirconium dichloride, dimethylsilylene bis(2-(2-(5-t-butyl)-thienyl)-4,5-benzoindenyl) zirconium dichloride, dimethylsilylene bis(2-(2-(5-trimethylsilyl)-thienyl)-4,5-benzoindenyl) zirconium dichloride, dimethylsilylene bis(2-(2-(5-phenyl)-thienyl)-4,5-benzoindenyl) zirconium dichloride, dimethylsilylene bis(2-(2-(5-methyl)-furyl)-4-phenyl-dihydroazulenyl) zirconium dichloride, dimethylsilylene bis(2-(2-(5-t-butyl)-furyl)-4-phenyl-dihydroazulenyl) zirconium dichloride, dimethylsilylene bis(2-(2-(5-trimethylsilyl)furyl)-4-phenyl-dihydroazulenyl) zirconium dichloride, dimethylsilylene bis(2-(2-(5-phenyl)-furyl)-4- phenyl-dihydroazulenyl) zirconium dichloride, dimethylsilylene bis(2-(2-(5-methyl)-thienyl)-4-phenyl-dihydroazulenyl) zirconium dichloride, dimethylsilylene bis (2-(2-(5-t-butyl)-thienyl)-4-phenyl-dihydroazulenyl) zirconium dichloride, dimethylsilylene bis(2-(2-(5-trimethylsilyl)-thienyl)-4-phenyl-dihydroazulenyl) zirconium dichloride and dimethylsilylene bis(2-(2-(5-phenyl)-thienyl)-4-phenyl-dihydroazulenyl) zirconium dichloride.

2. The metallocene compound according to claim 1, which is selected from the group consisting of dimethylsilylene bis(2-(2-(5-methyl)-furyl)-indenyl) zirconium dichloride, dimethylsilylene bis(2-(2-(5-t-butyl)-furyl)-indenyl) zirconium dichloride, dimethylsilylene bis(2-(2-(5-trimethylsilyl)-furyl)-indenyl zirconium dichloride, and dimethylsilylene bis(2-(2-(5-phenyl)-furyl)-indenyl) zirconium dichloride.

3. The metallocene compound according to claim 1, which is selected from the group consisting of dimethylsilylene bis(2-(2-(5-methyl)-thienyl)-indenyl) zirconium dichloride, dimethylsilylene bis-(2-(2-(5-t-butyl)-thienyl)-indenyl) zirconium dichloride, dimethylsilylene bis(2-(2-(5-trimethylsilyl)-thienyl)-indenyl) zirconium dichloride, and dimethylsilylene bis-(2-(2-(5-phenyl)-thienyl)-indenyl) zirconium dichloride.

4. The metallocene compound according to claim 1, which is selected from the group consisting of dimethylsilylene bis(2-(2-(5-methyl)-furyl)-4-phenyl-indenyl) zirconium dichloride, dimethylsilylene bis(2-(2-(5-t-butyl)-furyl)-4-phenyl-indenyl) zirconium dichloride, dimethylsilylene bis(2-(2-(5-trimethylsilyl)-furyl)-4-phenyl-indenyl) zirconium dichloride, and dimethylsilylene bis(2-(2-(5-phenyl)-furyl)-4-phenyl-indenyl) zirconium dichloride.

5. The metallocene compound according to claim 1, which is selected from the group consisting of dimethylsilylene bis(2-(2-(5-methyl)-thienyl)-4-phenyl-indenyl), zirconium dichloride, dimethylsilylene bis(2-(2-(5-t-butyl)-thienyl)-4-phenyl-indenyl) zirconium dichloride, dimethylsilylene bis(2-(2-(5-trimethylsilyl)-thienyl)-4-phenyl-indenyl) zirconium dichloride, and dimethylsilylene bis(2-(2-(5-phenyl)-thienyl)-4-phenyl-indenyl) zirconium dichloride.

6. The metallocene compound according to claim 1, which is selected from the group consisting of, dimethylsilylene bis(2-(2-(5-methyl)-furyl)-4,5-benzoindenyl) zirconium dichloride, dimethylsilylene bis(2-(2-(5-t-butyl)-furyl)-4,5-benzoindenyl) zirconium dichloride, dimethylsilylene bis(2-(2-(5-trimethylsilyl)-furyl)-4,5-benzoindenyl) zirconium dichloride, and dimethylsilylene bis(2-(2-(5-phenyl)-furyl)-4,5-benzoindenyl) zirconium dichloride.

7. The metallocene compound according to claim 1, which is selected from the group consisting of dimethylsilylene bis(2-(2-(5-methyl)-thienyl)-4,5-benzoindenyl) zirconium dichloride, dimethylsilylene bis(2-(2-(5-t-butyl)-thienyl)-4,5-benzoindenyl) zirconium dichloride, dimethylsilylene bis(2-(2-(5-trimethylsilyl)-thienyl)-4,5-benzoindenyl) zirconium dichloride, and dimethylsilylene bis(2-(2-(5-phenyl)-thienyl)-4,5-benzoindenyl) zirconium dichloride.

8. The metallocene compound according to claim 1, which is selected from the group consisting of dimethylsilylene bis(2-(2-(5-methyl)-furyl)-4-phenyl-dihydroazulenyl) zirconium dichloride, dimethylsilylene bis (2-(2-(5-t-butyl)-furyl)-4-phenyl-dihydroazulenyl) zirconium dichloride, dimethylsilylene bis(2-(2-(5-trimethylsilyl)furyl)-4-phenyl-dihydroazulenyl) zirconium dichloride, and dimethylsilylene bis(2-(2-(5-phenyl)-furyl)-4-phenyl-dihydroazulenyl) zirconium dichloride.

9. The metallocene compound according to claim 1, which is selected from the group consisting of dimethylsilylene bis(2-(2-(5-methyl)-thienyl)-4-phenyl-dihydroazulenyl) zirconium dichloride, dimethylsilylene bis (2-(2-(5-t-butyl)-thienyl)-4-phenyl-dihydroazulenyl) zirconium dichloride, dimethylsilylene bis(2-(2-(5-trimethylsilyl)-thienyl)-4-phenyl-dihydroazulenyl) zirconium dichloride, and dimethylsilylene bis(2-(2-(5-phenyl)-thienyl)-4-phenyl-dihydroazulenyl) zirconium dichloride.

* * * * *